(12) United States Patent
Cunningham

(10) Patent No.: US 8,947,656 B2
(45) Date of Patent: Feb. 3, 2015

(54) SMARTPHONE BIOSENSOR

(71) Applicant: The Board of Trustees of the University of Illinois, Urbana, IL (US)

(72) Inventor: Brian T. Cunningham, Champaign, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 0 days.

(21) Appl. No.: 13/801,978

(22) Filed: Mar. 13, 2013

(65) Prior Publication Data

US 2014/0193839 A1  Jul. 10, 2014

Related U.S. Application Data

(60) Provisional application No. 61/748,903, filed on Jan. 4, 2013.

(51) Int. Cl.
*G01J 3/28* (2006.01)
*G01J 3/44* (2006.01)
*G01N 21/63* (2006.01)

(52) U.S. Cl.
CPC .... *G01J 3/28* (2013.01); *G01J 3/44* (2013.01); *G01J 3/4406* (2013.01); *G01N 21/63* (2013.01)
USPC ...... 356/300; 356/301; 435/288.7; 422/82.05

(58) Field of Classification Search
CPC ... G01N 15/0205; G01N 23/06; G01N 23/02; G01N 33/50; G01N 33/5302; G01N 33/581; G01N 33/54366; B01L 2300/06; B01L 2219/0097; B01L 2219/00689; G02B 13/001; G06K 9/00127; G06F 19/30
See application file for complete search history.

(56) References Cited

U.S. PATENT DOCUMENTS 7,385,460 B1  6/2008  Wang et al.
7,479,404 B2  1/2009  Cunningham et al.
(Continued)

FOREIGN PATENT DOCUMENTS

WO  WO2010045949  * 7/2010

OTHER PUBLICATIONS

Abravaya et al., "Molecular Beacons as Diagnostic Tools: Technology and Applications," Clin. Chem. Lab. Med., 2003, pp. 468-474, vol. 41, Issue 4.
(Continued)

*Primary Examiner* — Melanie Y Brown
*Assistant Examiner* — Rebecca Martinez
(74) *Attorney, Agent, or Firm* — McDonnell Boehnen Hulbert & Berghoff LLP

(57) ABSTRACT

A mobile computing device that includes an image sensor may be used to detect the result of a biomolecular assay. The biomolecular assay may be performed in an optical assay medium that provides an optical output in response to light from a light source, with the optical output indicating result. A wavelength-dispersive element may be used to disperse the optical output into spatially-separated wavelength components. The mobile computing device may be positioned relative to the wavelength-dispersive element such that different wavelength components are received at different locations on the image sensor. With the mobile computing device positioned in this way, the image sensor may be used to obtain one or more images that include the separated wavelength components of the optical output. A wavelength spectrum of the optical output may be determined from the one or more images, and the result may be determined from the wavelength spectrum.

11 Claims, 18 Drawing Sheets

(56) References Cited

U.S. PATENT DOCUMENTS

| | | | |
|---|---|---|---|
| 7,521,769 | B2 | 4/2009 | Cunningham |
| 7,531,786 | B2 | 5/2009 | Cunningham et al. |
| 7,737,392 | B2 | 6/2010 | Cunningham et al. |
| 7,742,662 | B2 | 6/2010 | Cunningham |
| 7,968,836 | B2 | 6/2011 | Cunningham et al. |
| 8,889,424 | B2 | 11/2014 | Ehrenkranz et al. |
| 2006/0206010 | A1* | 9/2006 | Iida et al. ............... 600/300 |
| 2006/0222567 | A1* | 10/2006 | Kloepfer et al. ......... 422/68.1 |
| 2006/0279732 | A1* | 12/2006 | Wang et al. .............. 356/326 |
| 2008/0268548 | A1 | 10/2008 | Zuckerman |
| 2010/0035335 | A1 | 2/2010 | Lakowicz et al. |
| 2011/0130652 | A1 | 6/2011 | Boppart et al. |

OTHER PUBLICATIONS

Barhoumi et al., "Label-Free Detection of DNA Hybridization Using Surface Enhance Raman Spectroscopy," J. Am. Chem. Soc., 2010, pp. 12792-12793, vol. 132.

Behlke et al., "Fluorescence and Fluorescence Applications," Integrated DNA Technologies, 2005, pp. 1-13.

BioTEK Instruments, Inc., "An Introduction to Fluorescence Resonance Energy Transfer (FRET) Technology and its Application in Bioscience," www.biotek.com, Revised Jun. 15, 2005, pp. 1-8.

Block et al., "A detection instrument for enhanced-fluorescence and label-free imaging on photonic crystal surfaces," Optics Express, Jul. 20, 2009, pp. 13222-13235, vol. 17, No. 15.

Breslauer et al., "Mobile Phone Based Clinical Microscopy for Global Health Applications," PLoS One, Jul. 2009, pp. 1-7, vol. 4, Issue 7.

Chan et al., "A label-free photonic crystal biosensor imaging method for detection of cancer cell cytotoxicity and proliferation," Apoptosis, 2007, pp. 1061-1068, vol. 12.

Chan et al., "Self-referenced assay method for photonic crystal biosensors: Application to small molecule analytes," Sensors and Actuators B 120, 2007, pp. 392-398.

Choi et al., "Label-Free Photonic Crystal Biosensor Integrated Microfluidic Chip for Determination of Kinetic Reaction Rate Constants," IEEE Sensors Journal, Dec. 2009, pp. 1697-1704, vol. 9, No. 12.

Choi et al., "Single-step fabrication and characertization of photonic crystal biosensors with polymer microfluidic channels," Lab Chip, 2006, pp. 1373-1380, vol. 6.

Choi et al., "A 96-well microplate incorporating a replica molded microfluidic network integrated with photonic crystal biosensors for high throughput kinetic biomolecular interaction analysis," Lab Chip, 2007, pp. 1-8, vol. 7.

Cunningham et al., "Advantages and application of label-free detection assays in drug screening," Expert Opin. Drug Discov., 2008, pp. 891-901, vol. 3, No. 8.

Dai et al., "Surface-patterned microgel-tethered molecular beacons," Soft Matter, 2012, pp. 3067-3076, vol. 8.

Dasso et al., "A comparison of ELISA and flow microsphere-based assays for quantification of immunoglobulins," Journal of Immunological Methods, 2002, pp. 23-33, vol. 263.

de Souza et al., "Sensitivity and specificity of three ELISA-based assays for discriminating primary from secondary acute dengue virus infection," Journal of Clinical Virology, 2007, pp. 230-233, vol. 39.

Fologea, Daniel, "Detecting Single Stranded DNA with a Solid State Nanopore," Nano Letters, 2005, pp. 1905-1909, vol. 5, No. 10.

Guo, Xiaowei, "Surface plasmon resonance based biosensor technique: A review," J. Biophotonics, 2012, pp. 483-501, vol. 5, No. 7.

He, Lin et al., "Colloidal Au-Enhanced Surfce Plamson Resonance for Ultrasensitive Detection of DNA Hybridization," J. Am. Chem. Soc., 2000, pp. 9071-9077, vol. 122.

Homola et al., "Multi-analyte surface plasmon resonance biosensing," Methods, 2005, pp. 26-36, vol. 37.

Jameson et al., "Fluorescence Polarization/Anisotropy in Diagnostics and Imaging," Chem. Rev., 2010, pp. 2685-2708, vol. 110.

Kausaite-Minkstimiene et al., "Surface plasmon resonance biosensor for direct detection of antibodies against human growth hormone," Analyst, 2009, pp. 2051-2057, vol. 134.

Kim, Youngmi et al., "Molecular Beacons in Biomedical Detection and Clinical Diagnosis," Int J Clin Exp Pathol, 2008, pp. 105-116, vol. 1.

Lee, Mindy et al., "Two-dimensional silicon photonic crystal based biosensing platform for protein detection," Optics Express, Apr. 16, 2007, pp. 4530-4535, vol. 15, No. 8.

Leng et al., "ELISA and Multiplex Technologies for Cytokine Measurement in Inflammation and Aging Research," Journal of Gerontology: Medical Sciences, 2008, pp. 879-884, vol. 63A, No. 8.

Lin, Bo et al., "A label-free optical technique for detecting small molecule interactions," Biosensors and Bioelectronics, 2002, pp. 827-834, vol. 17.

Löfås et al., "Bioanalysis with surface plasmon resonance," Sensors and Actuators B, 1991, pp. 79-84, vol. 5.

Lu, M. et al., "Label free biosensor incorporating a replica-molded, vertically emitting distributed feedback laser," Applied Physics Letters, 2008, pp. 261502-1 to 261502-3, vol. 92.

Lyon et al., "Colloidal Au-Enhanced Surface Plasmon Resonance Immunosensing," Anal. Chem., 1998, pp. 5177-5183, vol. 70.

Martinez et al., "Simple Telemedicine for Developing Regions: Camera Phones and Paper-Based Microfluidic Devices for Real-Time, Off-Site Diagnosis," Anal. Chem., 2008, pp. 3699-3707, vol. 80, No. 10.

Mudanyali et al., "Integrated rapid-diagnostic-test reader platform on a cellphone," Lab Chip, 2012, pp. 2678-2686, vol. 12.

Nasir et al., "Development of a Fluorescence Polarization Assay for the Determination of Aflatoxins in Grains," J. Agric. Food Chem., 2002, pp. 3116-3121, vol. 50.

Nielson et al., "Fluorescence Polarization Immunoassay: Detection of Antibody to *Brucella abortus*," Methods, 2000, pp. 71-76, vol. 22.

Özkumur et al., "Quantification of DNA and Protein Adsorption by Optical Phase Shift," Biosens Bioelectron, Sep. 15, 2009, pp. 167-172, vol. 25, No. 1.

Pérez et al., "PocketELISA: A Low-Cost Portabel ELISA Reader Based on Image Analysis over PDA Platform for Clinical Diagnose in Medical Veterinary," IEEE International Symposium on Industrial Electronics, 2008, pp. 939-943.

Quinn et al., "Development and Application of Surface Plasmon Reseonance-Based Biosensors for the Detection of Cell-Ligand Interactions," Analytical Biochemistry, 2000, pp. 135-143, vol. 281.

Ray, Sandipan et al., "Label-free detection techniques for protein microarrays: Prospects, merits and challenges," Proteomics, 2010, pp. 731-748, vol. 10.

Rossi et al., "Analysis of protein-ligand interactions by fluorescence polarization," Nature Protocols, 2011, pp. 365-397, vol. 6, No. 3.

Skivesen et al., "Protonic-crystal waveguide biosensor," Optics Express, Mar. 19, 2007, pp. 3169-3176, vol. 15, No. 6.

Smith, Zachary J. et al., "Cell-Phone-Based Platform for Biomedical Device Development and Education Applications," PLoS ONE, Mar. 2011, pp. 1-11, vol. 6, Issue 3.

Soelberg et al., "Surface Plasmon Resonance Detection Using Antibody-Linked Magnetic Nanoparticles for Analyte Capture, Purification, Concentration, and Signal Amplification," Anal. Chem., 2009, pp. 2357-2363, vol. 81.

Threm et al., "Photonic crystal biosensors towards on-chip integration," J. Biophotonics, 2012, pp. 601-616, vol. 5, No. 8-9.

Tseng et al., "Lensfree microscopy on a cellphone," Lab Chip, Jul. 21, 2010, pp. 1787-1792, vol. 10, No. 14.

Tyagi et al., "Multicolor molecular beacons for allele discrimination," Nature Biotechnology, Jan. 1998, pp. 49-53, vol. 16.

Wu, Yan-Yun et al., "Limitations on the quantitative determination of telomerase activity by the electrophoretic and ELISA based TRAP assays," Clinica Chimica Acta, 2000, pp. 199-212, vol. 293.

Yao, Gang et al., "Molecular-beacon-based array for sensitive DNA analysis," Analytical Biochemistry, 2004, pp. 216-223, vol. 331.

Zhang, Wei et al., "High sensitivity photonic crystal biosensor incorporating nanorod structures for enhanced surface area," Sensors and Actuators B, 2008, pp. 279-284, vol. 131.

Zhu et al., "Quantum dot enabled detection of *Escherichia coli* using a cell-phone," Analyst, 2012, pp. 2541-2544, vol. 137.

(56) References Cited

OTHER PUBLICATIONS

Zhu et al., "Optofluidic Fluorescent Imaging Cytometry on a Cell Phone," Analytical Chemistry, 2011, pp. 6641-6647, vol. 83.

Zhu et al., "Cost-effective and compact wide-field fluorescent imaging on a cell-phone," Lab Chip, 2011, pp. 315-322, vol. 11.
International Search Report and Written Opinion for PCT/US2013/077416 mailed Apr. 30, 2014, 11 pages.

* cited by examiner

SMARTPHONE BIOSENSOR

PRIORITY

This application claims priority under 35 U.S.C. §119(e) to U.S. Provisional Application No. 61/748,903 filed Jan. 4, 2013, the content of which is incorporated by reference herein.

BACKGROUND

Since their introduction in 1997, "smartphones" have gained rapid market acceptance. Smartphones provide the user with advanced features in addition to being able to make voice calls. For example, smartphones typically have internet connectivity, high resolution cameras and touch-screen displays, and powerful CPUs. The rapid acceptance of smartphones has been driven by a combination of falling prices and increasingly sophisticated features. In addition, there is a growing ecosystem of applications that take advantage of smartphones' sensors, displays, and ability to connect to powerful computing and data storage capabilities that are available in the "cloud." The built-in capabilities of smartphones can be further extended through the addition of accessories that enable the phone to sense different types of information. For example, it is already possible to find commercial lens systems that enable the phone to be used as a rudimentary microscope with a 350× magnification, which is sufficient for capturing images of cells, bacteria, and biological tissue. Breslauer et al., *Plos One*, vol. 4, Jul. 22, 2009 and Smith et al., *Plos One*, vol. 6, Mar. 2, 2011. Smith et al. also demonstrated that, with addition of a light collimation system and a diffraction grating in front of the camera, a smartphone may function as a spectrometer with a wavelength resolution of 5 nm. The ability of a smartphone camera to take images of the colored label components of a biological assay have been applied to lateral flow immunoassays (Mudanyali et al., *Lab Chip*, vol. 12, pp. 2678-86, 2012), quantum-dot labeling of bacteria (Zhu et al., *Analyst*, vol. 137, pp. 2541-2544, 2012), and fluorescence microscopy (Breslauer et al.). Further, smartphone cameras have recently been exploited for microfluidic and optofluidic applications (Martinez et al, *Analytical Chemistry*, vol. 80, pp. 3699-3707, May 15, 2008 and Zhu et al., *Analytical Chemistry*, vol. 83, pp. 6641-6647, Sep. 1, 2011) and as a lens-free microscopy tool (Tseng et al., *Lab on a Chip*, vol. 10, pp. 1787-1792, 2010).

Such approaches, however, have not involved biomolecular assays with label-free detection. Detection of an analyte through one of its intrinsic physical properties (e.g., dielectric permittivity, mass, conductivity, or Raman scattering spectrum), called "label-free" detection, can be preferable for assay simplicity in terms of the number of reagents required, washing steps needed, and assay time Of all the label-free detection approaches that have been demonstrated, those based upon optical phenomena have been most commercially accepted due to a combination of sensitivity, sensor cost, detection system robustness, and high throughput. Adsorption of biomolecules, viral particles, bacteria, or cells on the surface of an optical biosensor transducer results in a shift in the conditions of optimal optical coupling, which can be measured by illuminating the transducer surface, and subsequently measuring a property of the reflected or transmitted light. Such a detection approach is extremely robust, and has become economically advantageous due to the advent of low cost light emitting diodes (LEDs), semiconductor lasers, and miniature spectrometers. For example, surface plasmon resonance (SPR) based biosensors and photonic crystal (PC) optical biosensors are capable of detecting broad classes of biological analytes through their intrinsic dielectric permittivity. Each approach has been implemented in the form of large laboratory instruments and miniaturized (shoebox-sized) systems. However, no prior label-free optical biosensor instrument has been fully integrated with a smartphone, using the camera in the phone itself as the detection instrument.

SUMMARY

In a first aspect, example embodiments provide a system comprising a light source, an optical assay medium configured to perform a biomolecular assay and provide an optical output in response to light form the light source, wherein the optical output is indicative of a result of the biomolecular assay, a wavelength-dispersive element, and a mobile computing device. The wavelength-dispersive element is configured to disperse the optical output into spatially-separated wavelength components. The mobile computing device includes an image sensor configured to receive at least a portion of the dispersed optical output such that different wavelength components are received at different locations on the image sensor.

The light source could be a broadband light source, such as an incandescent light bulb, sunlight, or an LED (either an LED on the smartphone or an external LED). Alternatively, the light source could be a narrow-band light source, such as a laser.

The wavelength-dispersive element could be a diffraction grating configured to diffract the optical output into at least one diffraction order in which different wavelength components of the optical output have different diffraction angles. Other types of wavelength-dispersive elements could also be used.

The system could include a mount for removably mounting the mobile computing device in a predetermined position relative to the wavelength-dispersive element and/or other optical components. The mobile computing device could be a smartphone, handheld computer, tablet computer, or other easily portable computing device. In some examples, the mobile computing device includes a display, a processor, a memory, and program instructions stored in the memory and executable by the processor to cause the mobile computing device to perform functions, such as: (i) using the image sensor to obtain at least one image of the spatially-separated wavelength components; (ii) determining a wavelength spectrum of the optical output based on the at least one image of the spatially-separated wavelength components; and (iii) displaying an indication of the wavelength spectrum on the display. The functions could further include determining the result of the biomolecular assay based on the wavelength spectrum and displaying an indication of the result on the display.

In some embodiments, the optical assay medium could include a photonic crystal (PC). The optical output could include light from the light source transmitted through the PC, with a wavelength spectrum having a local minimum in a range of wavelengths resonantly reflected by the PC. Alternatively, the optical output could include light from the light source reflected from the PC, with a wavelength spectrum having a local maximum in a range of wavelengths resonantly reflected from the PC. In either approach, the wavelengths that are resonantly reflected from the PC could be indicative of the result of the biomolecular assay.

In some embodiments, the optical assay medium could be configured to perform an optical absorption assay. For example, the optical assay medium could include a transparent container containing a composition for performing an enzyme-linked immunosorbent assay (ELISA) that produces a colored product in the presence of an analyte. Thus, the optical output could include light from the light source transmitted through the container, with a wavelength spectrum having an absorption feature related to absorption of light by the colored product. The intensity of the absorption feature could be indicative of the result of the biomolecular assay.

In some embodiments, the optical assay medium could include a fluorophore for performing a fluorescence assay. Thus, the optical output could include fluorescence emission from the fluorophore that is excited by light from the light source. The intensity of the fluorescence emission could be indicative of the result of the biomolecular assay. The fluorophore could be proximal to a surface, such as a photonic crystal, such that the fluorescence emission is enhanced. The optical assay medium could also include multiple fluorophores, such as a donor fluorophore and an acceptor fluorophore. Thus, the optical output could include fluorescence emission from the donor fluorophore and/or acceptor fluorophore that is excited by light from the light source. The intensity of the fluorescence emission from the donor fluorophore and/or acceptor fluorophore could be indicative of the result of the biomolecular assay.

In some embodiments, the optical assay medium could include a fluorophore for performing a fluorescence polarization assay. In such embodiments, the light source could be polarized, such as by using an inherently polarized light source or an unpolarized light source in conjunction with a polarizer. The optical output could include fluorescence emission from the fluorophore that is excited by light from the light source. The polarization of the fluorescence emission is indicative of the result of the biomolecular assay. To measure the polarization, the fluorescence emission could be passed through a polarizer that can be adjusted between two orthogonal polarizations, and the intensity of the fluorescence emission could be measured at the two orthogonal polarizations of the polarizer.

In some embodiments, the optical assay medium could include a surface configured for surface-enhanced Raman scattering (SERS). Thus, the optical output could include Raman scattering of the light source by molecules proximal to the SERS surface. The intensity of the Raman scattering could be indicative of the result of the biomolecular assay.

In a second aspect, example embodiments provide a method. The method may involve the following: performing a bimolecular assay in an optical assay medium; exposing the optical assay medium to light from a light source to produce an optical output, wherein the optical output is indicative of a result of the biomolecular assay; dispersing the optical output into spatially-separated wavelength components; using an image sensor of a mobile computing device to obtain at least one image of at least a portion of the dispersed optical output; and determining the result of the biomolecular assay based on the at least one image. The result of the biomolecular assay could be determined by the mobile computing device by determining a wavelength spectrum of the optical output based on the at least one image and determining the result of the biomolecular assay based on the wavelength spectrum.

The method may further involve placing the optical assay medium in a sample chamber of an instrument, wherein the instrument includes an input optical path for directing light from the light source to the optical assay medium in the sample chamber and an optical output path for receiving the optical output from the optical assay medium in the sample chamber. The mobile computing device could be removably mounted to the instrument. Mounting the computing device to the instrument could involve optically coupling the image sensor of the mobile computing device to the optical output path. Mounting the computing device to the instrument could further involve coupling a light source on the mobile computing device, such as an LED, to the input optical path. Thus, exposing the optical assay medium to light from a light source could involve exposing the optical assay medium to light from the light source on the mobile computing device.

In a third aspect, example embodiments provide an optical instrument. The optical instrument comprises a sample chamber for receiving an optical assay medium, an input optical path for directing light from a light source to the optical assay medium in the sample chamber, an output optical path for receiving an optical output from the optical assay medium in the sample chamber, and a mount for removably mounting the mobile computing device to the instrument in a working position. In the working position, an image sensor of the mobile computing device is optically coupled to the optical output path.

The optical output path could include a diffraction grating configured to disperse the optical output into spatially-separated wavelength components. Thus, with the mobile computing device in the working position, the image sensor may receive at least a portion of the dispersed optical output such that different wavelength components are received at different locations on the image sensor. In addition, a light source on the mobile computing device (such as an LED) may be optically coupled to the input optical path when the mobile computing device is in the working position.

DETAILED DESCRIPTION

1. Overview

Figure 1A:
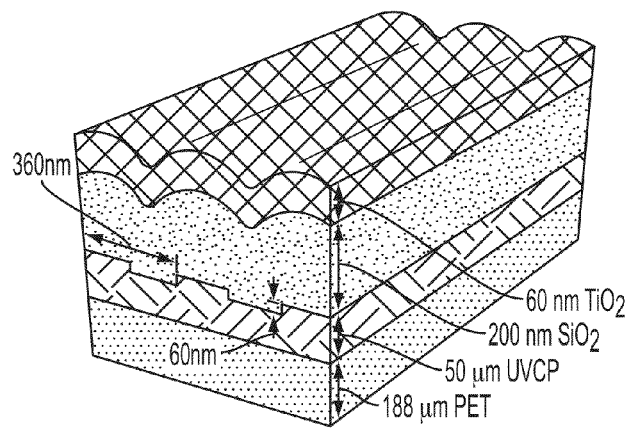
FIG. 1A is a cross-sectional schematic view of an example photonic crystal (PC) structure.

A mobile computing device (e.g., a smartphone) that includes an image sensor can be used as the detection instrument for various types of biomolecular assays. Such biomolecular assays may involve the qualitative or quantitative detection of DNA, RNA, nucleotides, proteins, or any other biologically relevant molecules. In an example embodiment, the mobile computing device is mounted to a special-purpose cradle that holds one or more optical components in alignment with the image sensor. With the mobile computing device properly mounted, the image sensor can be used to obtain one or more images from which the wavelength spectrum of an optical output of a biomolecular assay can be determined. In this way, the image sensor of a mobile computing device can perform the function of a high resolution spectrometer and wavelength filter.

The biomolecular assay may be performed in an optical assay medium that is illuminated using either a light source on the mobile computing device, such as a light emitting diode (LED), or an external light source, such as a light bulb, LED, or laser. In response to this illumination, the optical assay medium provides an optical output with a wavelength spectrum that can be detected by the image sensor on the mobile computing device. For example, a diffraction grating or other wavelength-dispersive element may be used to disperse the optical output into spatially-separated wavelength components such that different wavelength components are received at different locations on the image sensor.

In some embodiments, the optical assay medium may include a label-free optical biosensor, such as a photonic crystal biosensor, resonant waveguide grating biosensor, surface plasmon resonant biosensor, or other type of optical biosensor. In some embodiments, the optical assay medium may include a fluorophore or multiple fluorophores (e.g., a donor fluorophore and an acceptor fluorophore) for performing a fluorescent assay. The fluorescent assay could be either homogenous (e.g., a fluorescence polarization assay) or surface-based. For example, the optical assay medium may include a surface, such as a photonic crystal, that enhances the fluorescence output. Liquid-based fluorescent assays could also be used to detect fluorescence resonance energy transfer (FRET), fluorescent particles (e.g., microparticles or nanoparticles), or fluorescent molecular beacons. In some embodiments, the optical assay medium may include a composition for performing an optical absorption assay, such as an enzyme-linked immunosorbent assay (ELISA). In some embodiments, the optical assay medium may include a surface for performing surface-enhanced Raman scattering. The optical assay medium could perform other types of assays as well.

The use of a smartphone or other mobile computing device as the detection instrument for biomolecular assays allows inexpensive, portable, and multifunctional systems to perform biosensor assays in contexts outside the laboratory. Applications can include point-of-care diagnostic systems for measuring viral loads, nutritional status, disease biomarkers, or environmental contaminants in contexts where laboratory-based detection instruments are not possible. Such tests could be performed in the home, in global-health settings, in law enforcement and in clinics. The mobile computing device can also provide internet connectivity that allows sensor data to be easily combined with patient information and geographical location and interfaced with an external computation facility that can perform functions like data interpretation, mapping (for example, measuring the distributed characteristics of a population or a natural resource), construction of databases, and alerting of a remotely located medical expert for immediate feedback to the patient. Smartphone-based biosensor assays can allow tests that are currently only performed by trained technicians in laboratories to be performed by anyone by reducing the size and cost of the detection system.

2. Example Photonic Crystal Biosensors

Photonic crystal biosensors are described in U.S. Pat. Nos. 7,479,404, 7,521,769, 7,531,786, 7,737,392, 7,742,662, and 7,968,836, which patents are incorporated herein by reference. In general, a photonic crystal (PC) includes a thin film of a material with a high index of refraction on a one-dimensional or two-dimensional grating structure that is formed in a material with a low index of refraction. The grating dimensions, thin film thicknesses, and indices of refraction can be selected so that the structure behaves as a high efficiency narrowband reflectance filter with a resonance having a center wavelength and a resonance bandwidth.

FIG. 1A illustrates an example PC. In this example, a 1-dimensional grating structure is formed in a UV-curable polymer (UVCP) on a flexible plastic substrate (PET) by a nanoreplica molding process. The grating period is 360 nm and the grating depth is 60 nm. The polymer grating is overcoated with sputtered thin films of $SiO_2$ (200 nm thickness) and $TiO_2$ (60 nm thickness, refractive index=2.35). After fabrication, the flexible plastic substrates of one or more PCs can be attached to a carrier, such as a glass microscope slide, using double-sided pressure-activated adhesive film. In this way, a standard 1 inch×3 inch glass microscope slide can accommodate multiple PCs (e.g., 21 PCs in a 3×7 array).

Figure 1B:
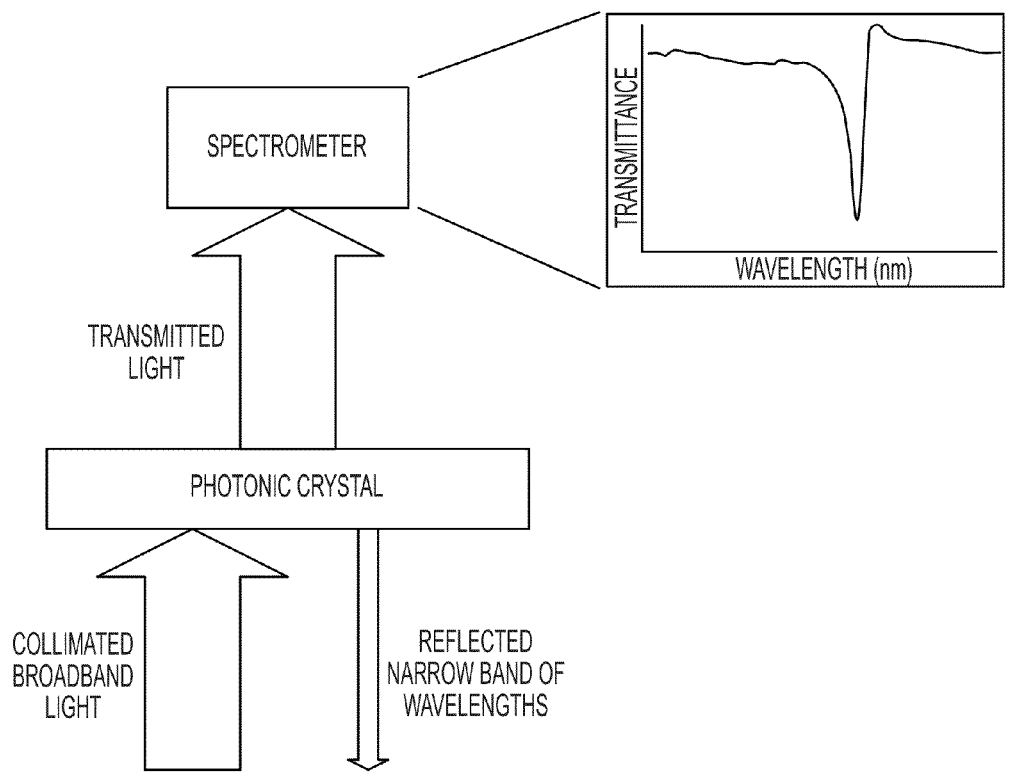
FIG. 1B is a diagram that illustrates the operating principle of a PC according to an example embodiment.

Depending on the structure of the PC, the center wavelength could be in the infrared, visible, or ultraviolet. With the center wavelength at 565 nm, the resonance bandwidth could have a full width at half maximum (FWHM) of about 5 nm. The narrow band of resonantly reflected wavelengths could be reflected with over 95% efficiency. As a result, when the PC is illuminated by collimated light at normal incidence, all wavelengths may pass through the PC with little or no attenuation, except for the narrow band of resonantly reflected wavelengths. This principle is illustrated in FIG. 1B, which shows a transmission spectrum with a sharp dip that corresponds to the narrow band of resonantly reflected wavelengths. Adsorption of materials, such as biomolecules, viral particles, bacteria, or cells, on the PC surface results in an increase of the effective refractive index of the resonant mode. This creates a positive shift in the wavelength of resonant reflection, the magnitude of which is proportional to the optical density of the adsorbed material. Therefore, a measurable shift of the peak wavelength value (PWV) of minimum transmission efficiency (or equivalently a maximum in reflection efficiency) can occur as a result of a biological assay.

3. Example Smartphone Cradle Optical System

Figure 2A:
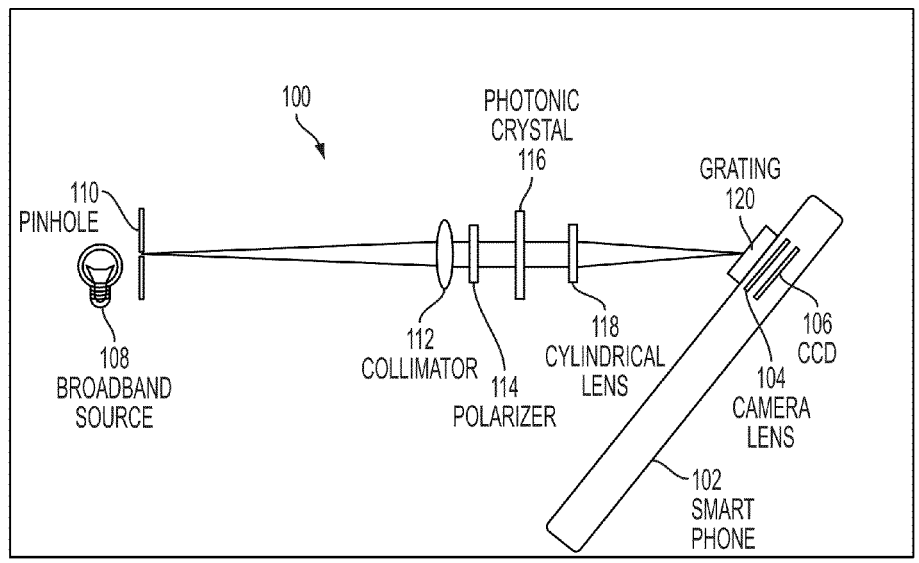
FIG. 2A is a schematic diagram showing the optical components of an example smartphone detection system.

FIG. 2A is a schematic diagram illustrating an example detection system 100 that includes a smartphone 102 with a digital camera. As shown in FIG. 2A, the digital camera includes a camera lens 104 and an image sensor (CCD) 106. Unpolarized light from a broadband light source 108 (such as an incandescent lamp, LED, or sunlight) passes through a pinhole 110 (diameter=100 microns), a collimator 112 (a lens with a focal length of 75 mm), and a linear polarizer 114, so as to be incident upon a photonic crystal (PC) 116 mounted to a glass microscope slide. The linear polarizer 114 is oriented to pass only light with its electric field vector perpendicular to the grating lines in PC 116. The collimated and polarized light passes through the PC 116 at normal incidence, so all the incident light may pass forward, with the exception of the PC resonant wavelength band. A slot for the PC 116 can be incorporated into the optical chain, to facilitate its insertion and removal. Small markings can be made on the PC slide, so a specific location can be re-measured during distinct steps in the assay process. After passing through the PC 116, the light is focused to a line by a cylindrical lens 118 (focal length=50 mm), onto the entrance pupil of the smartphone's camera. A diffraction grating 120 (1200 lines/mm) placed between the cylindrical lens and the camera disperses the wavelength components of the light across the camera's image sensor (CCD 106). In this example, the optical path is set at an angle of ~47° with respect to the camera face so that the camera receives the grating's first order.

Figure 2B:
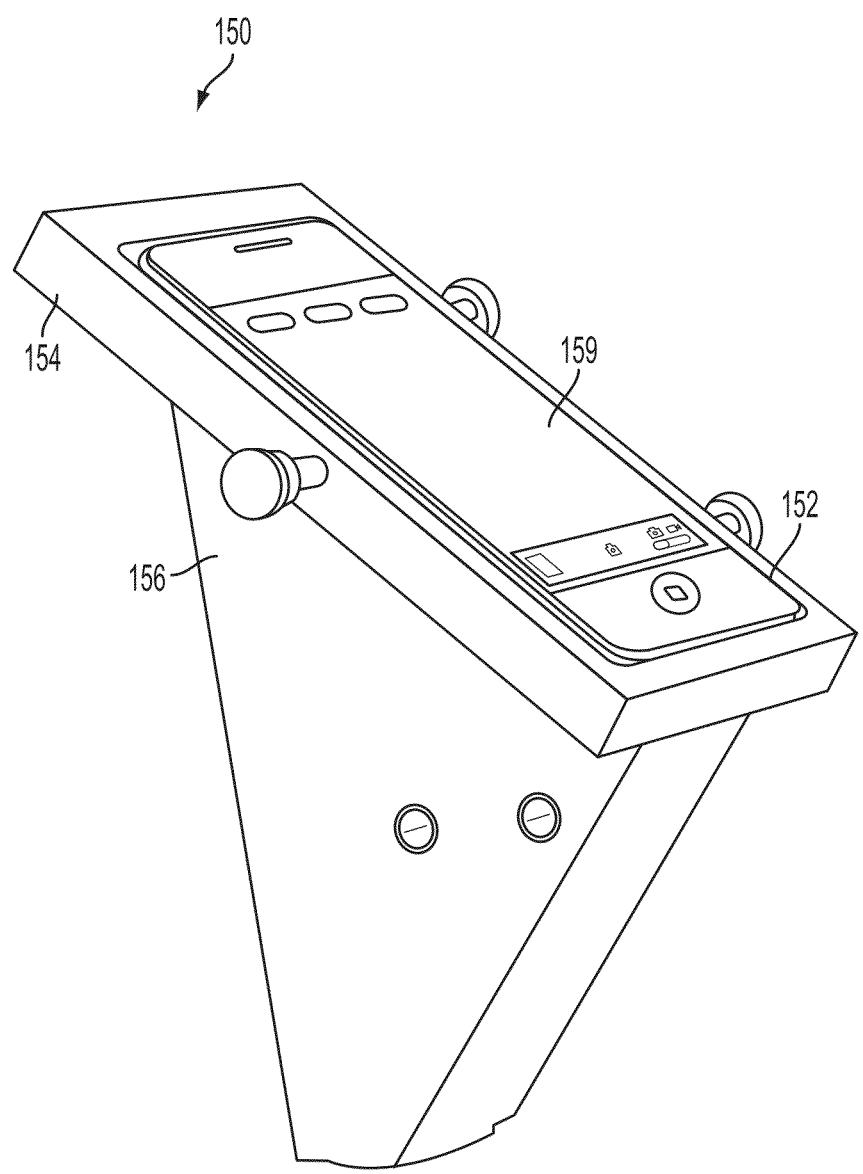
FIG. 2B is a diagram showing a view of an example cradle with a smartphone mounted thereto.
Figure 3A:
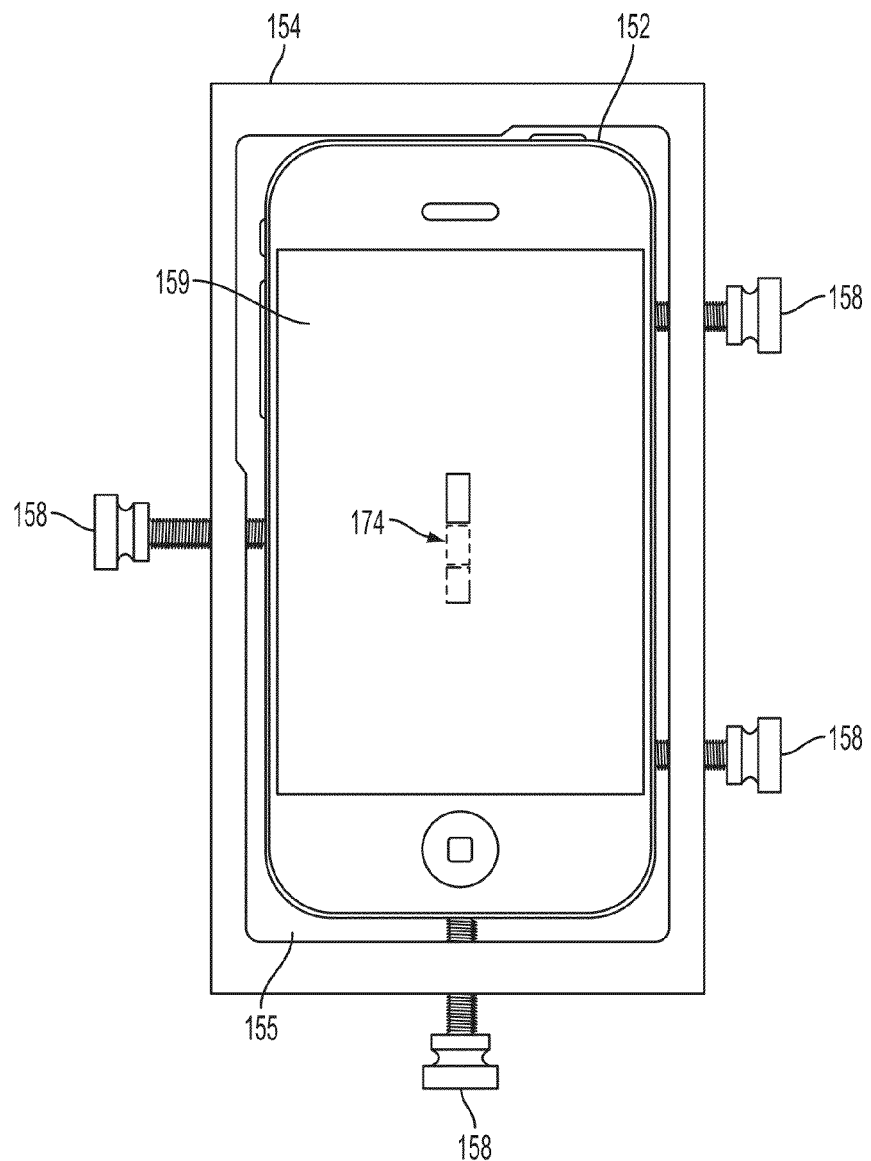
FIG. 3A is a diagram showing another view of the cradle of FIG. 2B.
Figure 3B:
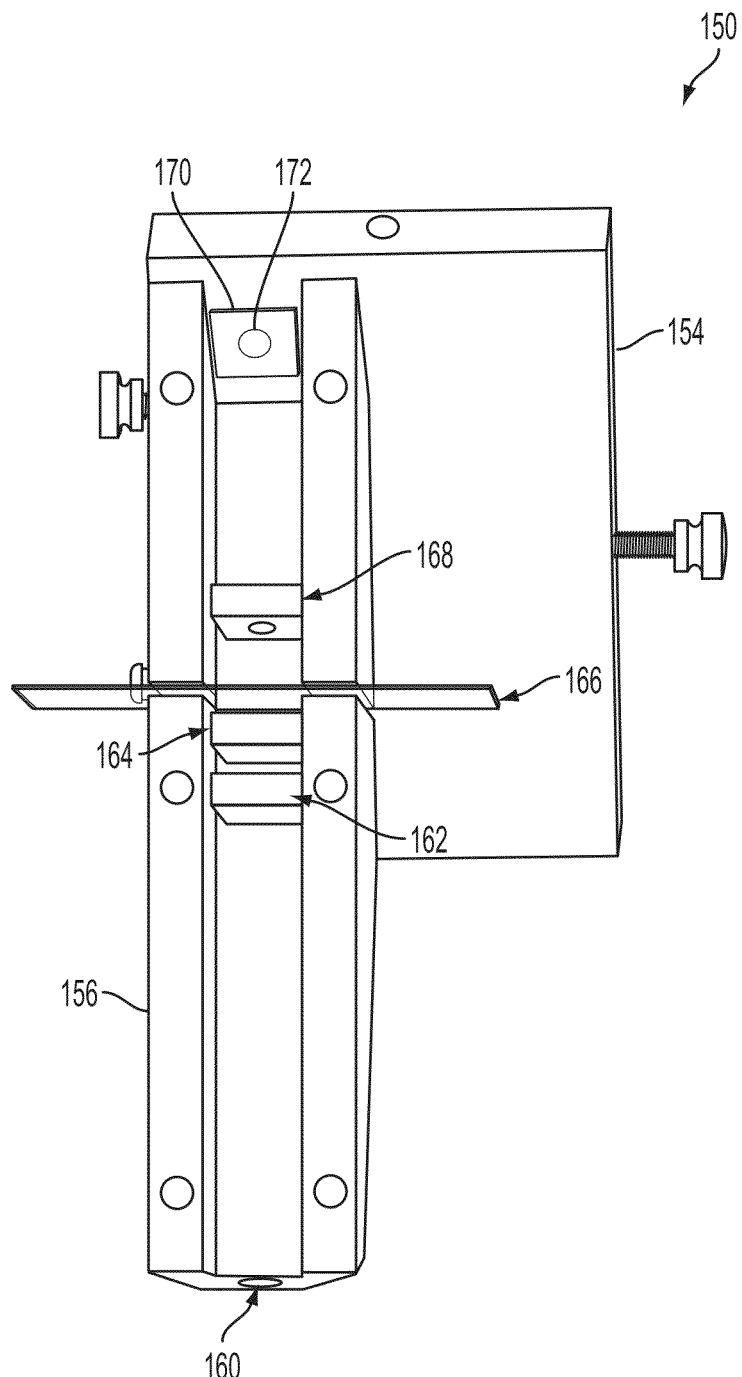
FIG. 3B is a diagram showing the internal optical components of the cradle of FIG. 2B.

To position the smartphone 102 so that its digital camera receives the first order of the diffraction grating 120, the smartphone can be removably mounted to a cradle. FIGS. 2B, 3A, and 3B illustrate an example cradle 150 that could be used. FIG. 2B is a side view of the cradle 150 with a smartphone 152 mounted thereto. In this example, smartphone 152 is an iPhone 4 (Apple, Inc.). It is to be understood, however, that other smartphones or other types of mobile computing device could be used. The cradle 150 shown in FIG. 2B was made of anodized machined aluminum. Alternatively, the cradle 150 could be made of injection molded plastic or other structural materials. The cradle 150 includes a mounting portion 154 for mounting the smartphone 152 and also includes a light-sealed optical housing 156 that houses optical components.

FIG. 3A shows the mounting portion 154 in more detail. The mounting portion 154 includes a recess 155 into which smartphone 152 can be fitted. The smartphone 152 may be secured in place in recess 155 through the use of mounting screws 158. Smartphone 152 is mounted in recess 155 with its user interface 159 facing out, as shown. Thus, in the mounted position, user interface 159 (which includes a display and a touchscreen interface) is accessible and smartphone 152 can be operated, for example, to obtain images using its image sensor. The image sensor is on the underside of smartphone 152 and, thus, is not shown in FIG. 3A.

FIG. 3B shows the back of cradle 150 with the light seal of optical housing 156 removed to show the optical components housed therein. In this example, the optical components are as described above for FIG. 2A, except that an external light source is used. Thus, light from the external light source enters cradle 150 through a pinhole 160 and then passes through a collimator 162, a polarizer 164, a PC 166 (mounted on a glass slide), a cylindrical lens 168, and a diffraction grating 170. The light in the first order of diffraction grating 170 enters recess 156 through a hole 172 to reach the image sensor on the smartphone 152.

When the pinhole 160 is illuminated with light from a broadband source (e.g., a tungsten incandescent lamp) with PC 166 removed, the broadband light is dispersed by diffraction grating 170 and appears in a digital image obtained by smartphone 152 as a spectrum band that includes the entire visible spectrum (i.e., wavelengths from about 400 nm to about 650 nm) in a "rainbow" type pattern. FIG. 3A shows an example spectrum band 174 (not shown in color) displayed on user interface 159 of smartphone 152. Although the iPhone4 image sensor has a total of 5 megapixels (2592×1936), the spectrum band covers approximately 800 pixels in the dispersive direction. With a pinhole 160 of approximately 100 microns, the cylindrical lens 168 produces a focused line with a width of roughly 100 pixels for each wavelength. Assuming a focal length of the iPhone4 lens of 4.3 mm, the wavelength separation between adjacent pixels in the spectral direction will be about 0.34 nm/pixel.

Figure 4A:
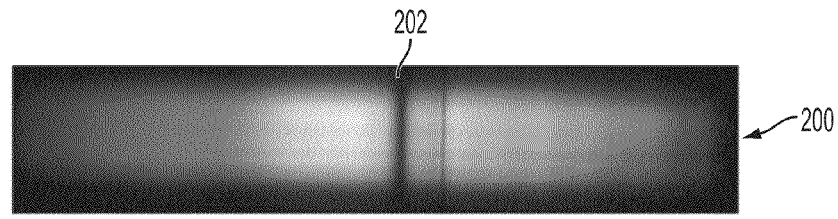
FIG. 4A shows an example wavelength spectrum as it may be displayed on a smartphone.
Figure 4B:
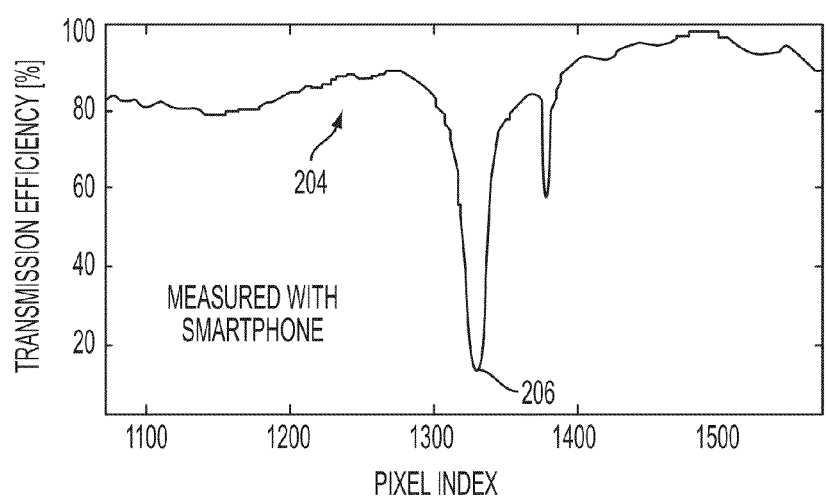
FIG. 4B is a graph of the wavelength spectrum of FIG. 4A.

When PC 166 is inserted into the optical path, a narrow band of wavelengths corresponding to the wavelengths resonantly reflected by PC 166 is removed from the transmitted light, resulting in a dark band that can be observed in the spectrum band. FIG. 4A illustrates an example spectrum band 200 that includes a dark band 202 resulting from resonant reflection from a PC. FIG. 4B is a graph 204 showing the variation in intensity (corresponding to transmission efficiency through PC) in the spectrum band 200 along the dispersive direction. The graph 204 clearly shows a sharp dip 206 in the transmission efficiency that corresponds to the dark band 202 that can be observed in the spectrum band 200. With appropriate calibration, the pixel indices in the graph 204 can be correlated to wavelengths, so as to enable determination of the peak wavelength value (PWV) of the dip 206.

4. Example Mobile Computing Device

Figure 5:
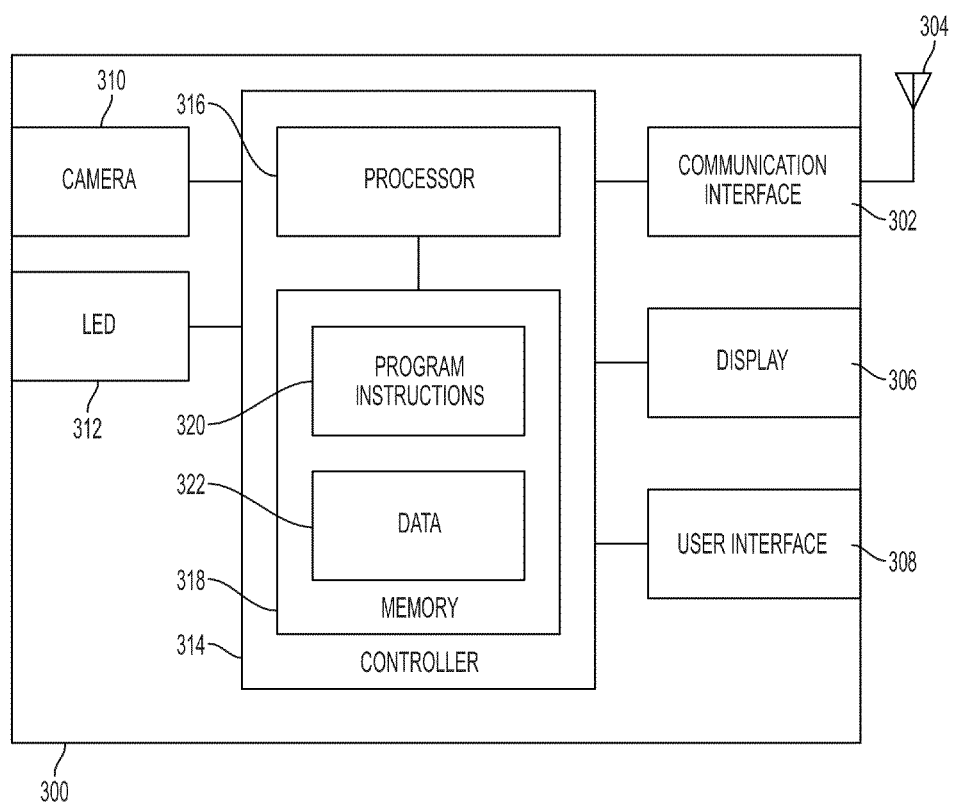
FIG. 5 is a block diagram of an example mobile computing device.
Figure 6A:
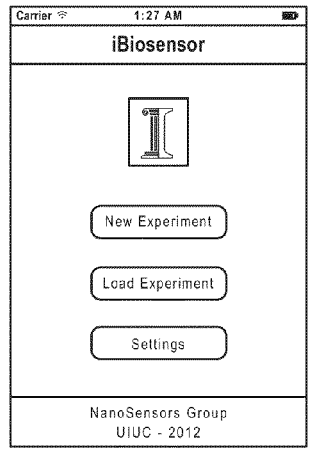
FIGS. 6A-6E show screen views of an example smartphone application.
Figure 6B:
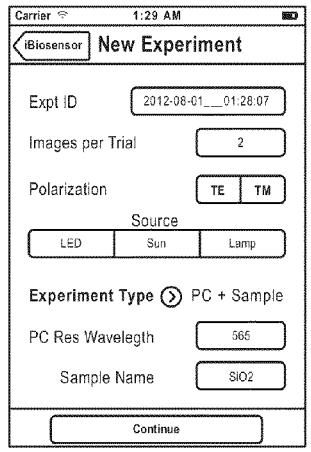
Figure 6C:
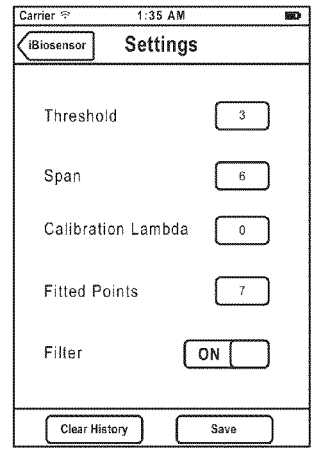
Figure 6D:
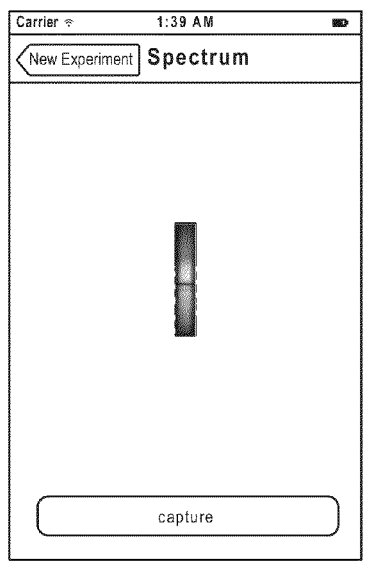
Figure 6E:
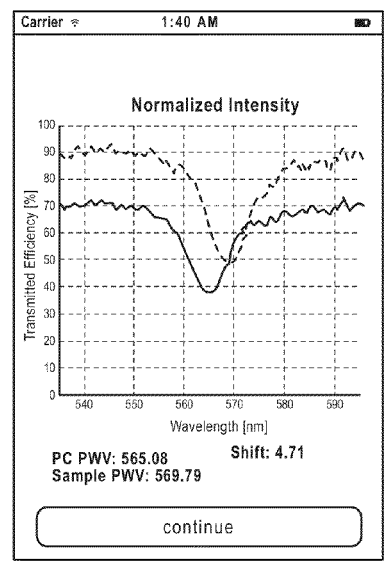

FIG. 5 is a block diagram illustrating an example mobile computing device 300. The mobile computing device 300 could be a smartphone, a handheld computer, a tablet computer, or other easily portable computing device. The mobile computing device 300 includes a communication interface 302 for wireless communication via an antenna 304. The wireless communication could involve sending or receiving voice, images, video, data, or other information. The wireless communication could use any type of wireless communication protocol, such as 3G or 4G cellular communication protocols, WiFi, or Bluetooth. Instead of or in addition to communication interface 302, the mobile computing device 300 may include a communication interface for communicating over USB, Ethernet, or other wired connections.

The mobile computing device 300 also includes a display 306 that can display text, images, graphics, or other visual information. A user may interact with the mobile computing device 300 via a user interface 308. The user interface 308 may include a touchscreen over the display 306. Alternatively or additionally, the user interface 308 may include a keypad, buttons, or other controls.

The mobile computing device 300 is able to capture still images and/or images through the use of a camera 310. The camera 310 includes a lens and an image sensor, such as a CCD. The camera 310 could be on a side of the mobile computing device 300 that is opposite the side that includes the display 306. The mobile computing device 300 may also include a light source, such as a white-light LED 312, next to the camera 310. The LED 312 may be intended for flash photography, for example.

The mobile computing device 300 may be controlled by a controller 314 that includes a processor 316 and a memory 318. The memory 318 could include random access memory (RAM), read-only memory (ROM), flash memory, or any other type of non-transitory media. The memory 318 may store program instructions 320 and data 322. The processor 316 may execute the program instructions 320 to cause the mobile computing device 300 to perform functions, which functions may use or generate data 322. The functions may involve communicating via the communication interface 302, displaying output on display 306, receiving user input via user interface 308, using camera 310 to obtain images, and/or controlling the illumination of LED 312. The program instructions 320 may include software for one or more applications (often known as "Apps") that can be accessed by a user.

5. Smartphone Biosensor Software App

An iPhone application (App) was developed to facilitate gathering of spectra, measuring the PWV of the PC, and determining PWV shifts, using a cradle such as cradle 150 described above. FIGS. 6A-6E are example screen views of the App. The App first prompts the user to enter information about a measurement, such as the sample name. Additional global settings can be adjusted by the user to control filtering parameters, intensity threshold, and the span of pixels from the center of the resonant band to be considered during curve fitting. To achieve the highest spectral resolution, the iPhone's camera is focused at infinity. This can be done by pointing the camera to a distant object in a well lit environment before placing the iPhone into the cradle. The App locks the focal distance of the camera at infinity for all subsequent measurements.

Tapping the "Capture" button within the App triggers the following events: A rapid sequence of spectra images (e.g., five spectra images) are captured consecutively to minimize the effects of small intensity fluctuations that arise from the light source and camera's sensor. To obtain an intensity spectrum profile from each spectra image, the App first crops the image to thirty pixels gathered from the center of the 100-pixel wide spectral band, discarding dark pixels above and below the band. The 30 pixel values taken from the band are averaged to yield a single intensity value for one wavelength of the spectrum for each of the consecutive images, resulting in a one dimensional array (1×2592 pixels) per image captured. The spectra gathered from independent consecutive images are finally averaged to yield a single spectrum. This process can take about two seconds. The App can also be calibrated to correlate pixel values with specific wavelength values.

The App stores the spectrum of the light source before a PC is inserted into the cradle. The spectrum of the light source is used to normalize the spectrum after the PC is inserted into the optical path to yield the PC transmission efficiency plot shown in FIG. 6E. It was found that the transmission spectrum for the PC measured with the smartphone system closely matches the transmission spectrum obtained by illuminating the PC with the collimated output of an optical fiber and measuring the transmission efficiency with a conventional spectrometer.

The App then processes the PC transmission spectrum to determine the PWV for the measurement. The App identifies the pixel in the spectrum with the lowest intensity value, and then uses the 20 pixel values surrounding this point to fit the "dip" to a third-order polynomial function. The PWV is mathematically determined as a local minimum of the polynomial. In this way, PWV shifts ~10× smaller than the wavelength increments of the camera can be measured. The App also enables wireless transmission of spectra and PWV measurements.

6. Example Measurements a. Measurement Protocol

Using the instrument (e.g., cradle 150 and smartphone 152) and software (e.g., the iPhone App described above), an assay can be performed as follows. The PC is initially prepared with a capture molecule (such as an antibody, aptamer, or single-strand DNA sequence) that selectively recognizes the analyte in a test sample. The sensor surface is further prepared with a "blocking" step that prevents nonspecific adsorption of other molecules. The PWV of the sensor is measured prior to exposure to the test sample to establish a baseline reading. Exposure of the sensor to the test sample results in adsorption of the analyte upon the PC, followed by rinsing/drying the sensor. A second PWV measurement is taken of the sensor, and the PWV shift is determined by subtraction of the baseline PWV. The basic approach outlined here can be augmented by the incorporation of positive and negative experimental controls, including the use of a "reference" sensor that is prepared with an unmatched capture molecule, but still exposed to the test sample. Thus, measurements can be taken with the PC surface in a dry state. Alternatively, the system can be further augmented via incorporation of a static liquid chamber or flow cell on the PC, so the PWV shifts can be monitored kinetically.

b. Wavelength Calibration

Figure 7:
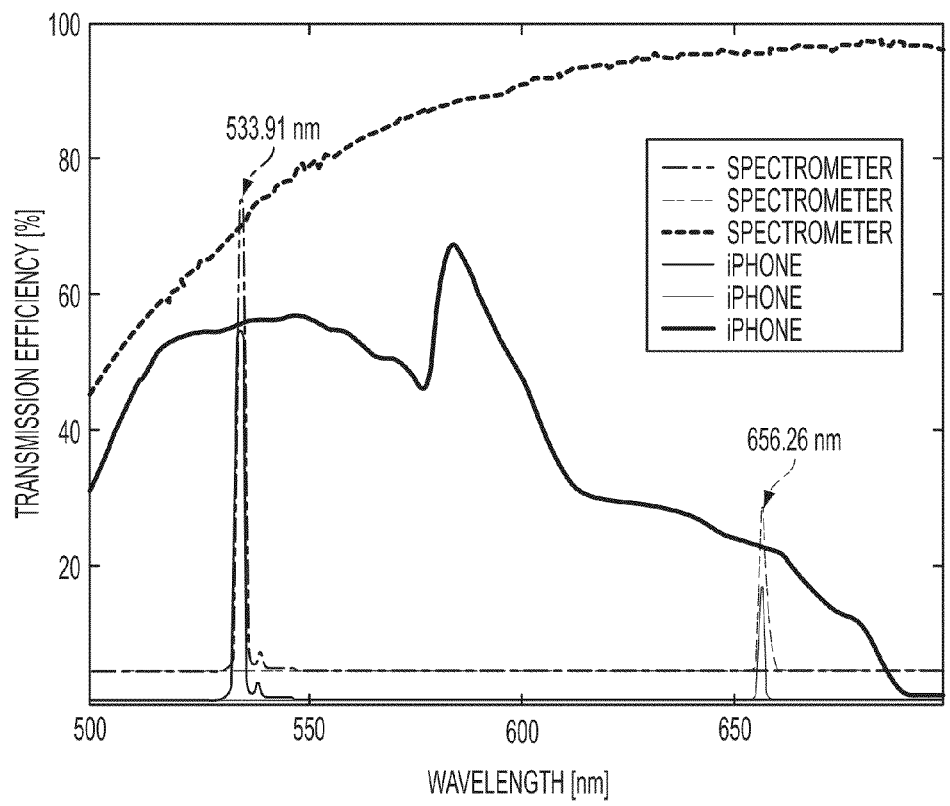
FIG. 7 shows spectra from a red laser pointer, a green laser pointer, and a tungsten lamp, as measured by a spectrometer and by a smartphone.

Pixel values in the smartphone image were translated to calibrate the wavelength values through the use of two laser pointers and a calibrated spectrometer (Ocean Optics HR2000). As shown in FIG. 7, a green and a red laser pointer were used to illuminate the tip of an optical fiber with its distal end connected to the spectrometer, resulting in the dashed curves with peak intensity values at wavelengths of $\lambda=533.91$ nm and $\lambda=656.26$ nm. The same laser pointers were then used to illuminate the pinhole of the instrument (i.e., pinhole 160 in cradle 150), resulting in the solid curves shown in FIG. 7. Assuming linearity between the image pixel value and wavelength with two known values of wavelength, it is possible to derive a transfer function that translates every pixel value into a wavelength value for all subsequent measurements. In this example, the index values in pixels are translated into a wavelength index through the conversion factor 0.334 nm/pixel.

Also shown in FIG. 7 is a comparison of the spectra from the tungsten lamp illumination source taken by the spectrometer and the smartphone. A drop off in intensity is observed as the wavelength increases beyond $\lambda=580$ nm and a complete loss of sensitivity to wavelengths greater than $\lambda=680$ nm can be attributed to an internal filter in the smartphone's camera. Thus, the PC can be designed for operation in the $550<\lambda<580$ nm range in order to take advantage of the wavelengths available with good sensitivity from the camera.

Figure 8:
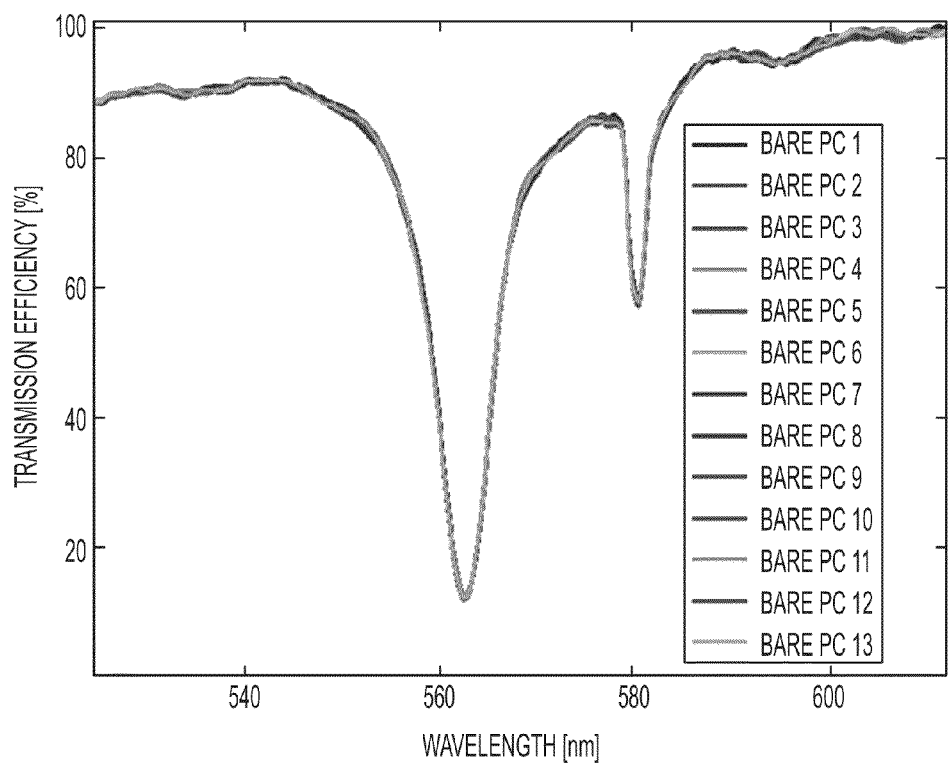
FIG. 8 shows 13 independent PC spectra.

Using the pixel-to-wavelength mapping described above, the repeatability of independent PWV measurements, when the PC is removed/reinserted from the cradle without intentionally introducing any other variable, was studied. FIG. 8 shows 13 overlaid spectra from of independent measurements when the PC is removed and replaced within the cradle, as would be the case when a biological assay is performed. The spectra are observed to have a mean PWV=565.07 nm, and a standard deviation of $\sigma=0.10$ nm, demonstrating that measurements are highly reproducible and that wavelength shifts greater than $3\sigma=0.30$ nm are statistically meaningful in the context of biological assays.

c. Example Measurements of PWV Shift

Figure 9:
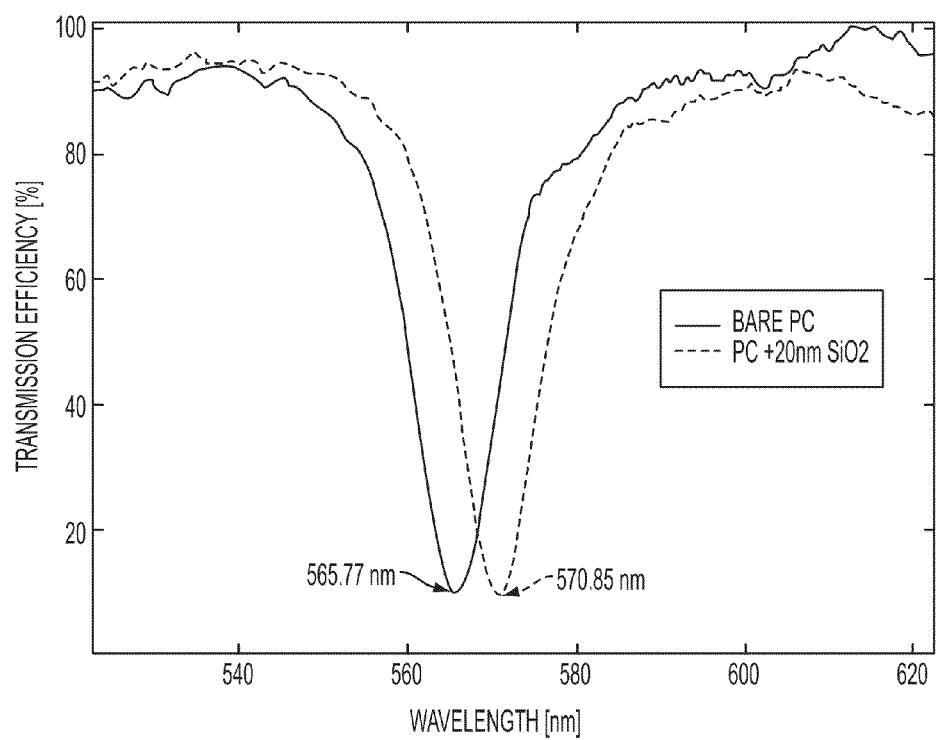
FIG. 9 shows normalized transmission characteristics for a bare PC and for an adjacent region of the same PC coated with a 20 nm $SiO_2$ film.

Shifts in the PC wavelength caused by addition of material to the PC surface were measured as follows. A PC mounted to a microscope slide was prepared by depositing a 20 nm thin film of $SiO_2$ by RF sputtering on one half of slide, while leaving the other half uncoated. Using a standard spectrometer, the PWV for the $SiO_2$ coated PC was measured and compared to the bare PC region. A PWV difference of 5.08 nm was observed. The transmission spectra for the same regions of the PC were determined using the smartphone detection system. FIG. 9 shows the spectra for the bare PC and the $SiO_2$-coated PC. The PWV for the bare PC was 565.77 nm, and the PWV for the $SiO_2$-coated PC was 570.85 nm. Thus, a PWV shift of 5.08 nm was measured using the smartphone detection system.

Figure 10:
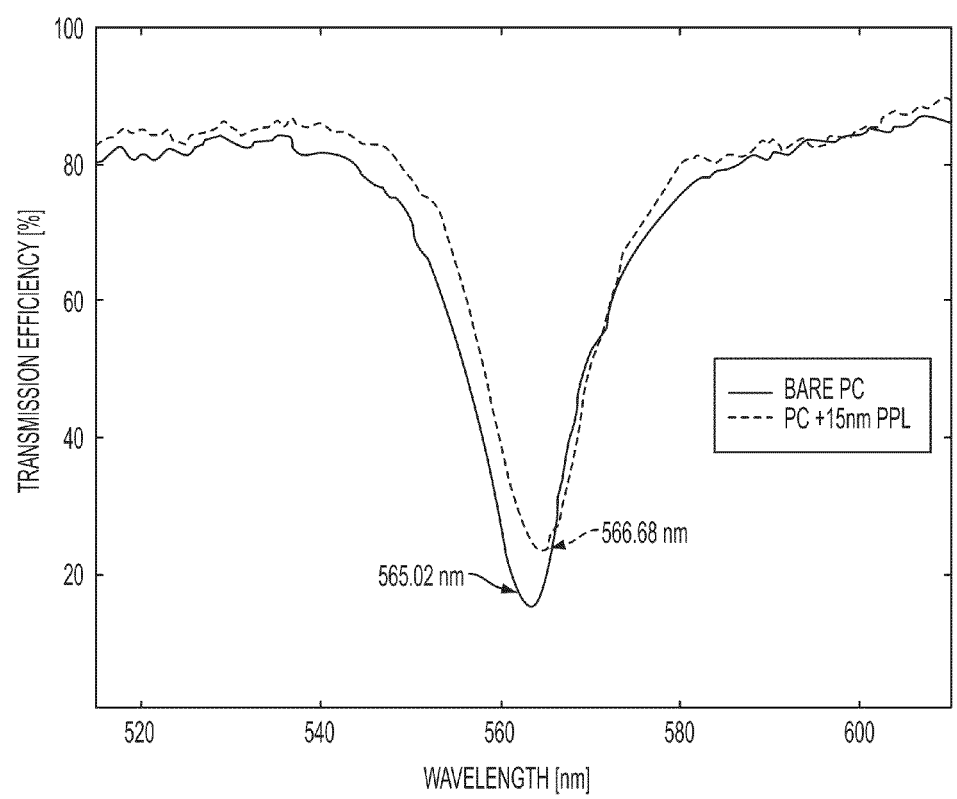
FIG. 10 shows transmission spectra of a PC before and after deposition of a monolayer of PPL protein.

The PWV shift induced by adsorption of a protein monolayer on a PC was also measured. The protein polymer polyphe-lysine (PPL) is well-known to adhere to dielectric surfaces, such as the PC, forming a 15 nm thick layer that self-limits to a single monolayer. A baseline spectrum from a specific location of a PC biosensor slide in its "bare" state was obtained. A temporary rubber gasket was then placed over that location to create a liquid-containment well. The well was filled with 100 μL of PPL (Sigma Aldrich) diluted in deionized water at a concentration of ~1 mg/ml, and allowed to incubate with the PC surface for 120 minutes at room temperature. After incubation, the PPL solution was removed and the well was flushed with deionized water. The gasket was removed, and the PC was further rinsed and dried with dry $N_2$ before returning the PC to the detection system for a second spectral measurement. Results of this experiment are shown in FIG. 10. The PWV for the bare PC was 565.02 nm, and the PWV for the PC with the PPL monolayer was 566.68 nm. Thus, a PWV shift of 1.66 nm was observed.

d. Example Biodetection

In an example biodetection experiment, an immobilized molecule on a PC surface is used to capture a molecule that is selectively recognized. As a representative example, the smartphone detection instrument was used to detect binding of a single-strand oligonucleotide sequence (20-mer) to an immobilized strand of its complementary sequence.

A PC mounted to a microscope slide was functionalized with an epoxysilane using a vapor deposition process as described below. Initially, the slide was washed in isopropanol and deionized (DI) water for two minutes, respectively. The PC was then dried under a stream of nitrogen ($N_2$) and subjected to a 100 Watt oxygen ($O_2$) plasma for 10 minutes at a pressure of 0.75 mTorr. Next, a vapor-deposition of 3-glycidoxypropyltrimethoxysilane (Gelest, Inc.) was performed in a 500 ml glass staining dish by transferring 100 μl of the silane to the dish and then placing a glass rack loaded with the device inside the dish. The dish was placed overnight in a vacuum oven at a temperature of 80° C. and a pressure of 30 Torr. The slide was then removed from the glass rack and sonicated in vertical staining jars of toluene, methanol and DI water for two minutes each and finally dried under a stream of nitrogen ($N_2$). Three squares, each 9×9 mm² in dimension, were drawn on the slide using a hydrophobic pen (Super HT Pap pen, Research Products International Corp), forming "wells" A to C. The spectrum of each well was recorded at this stage, and considered as the baseline of this experiment with an average PWV of 568.41 nm across all wells. Next, 100 μL of the amine-modified, capture oligonucleotide (IDT, Inc.), prepared at a concentration of 2 μM in 3× saline sodium citrate (SSC) buffer (Sigma Aldrich) was applied to each well and incubated overnight. The sequence of the capture oligonucleotide was 5'-/Amino Modifier/ATT-TCC-GCT-GGT-CGT-CTG-CA-3'.

After the incubation period, the PC was rinsed first in a solution of DI water with 0.2% by volume of SDS (Sigma Aldrich), followed by two rinses in DI water. The PC was then dried in a stream of $N_2$ and PWV readings were performed again on all wells. An average PWV of 577.53 nm was observed across the wells. Next, the complementary target oligonucleotide (IDT, Inc.) was applied to the PC in equal volumes of 100 μL per well but at three different concentrations of 1 μM (well A), 750 nMm (well B) and 250 nMm (well C). A negative control well with no target DNA was also created to record any non-specific shift. The target oligonucleotide sequence used was 5'-TGC-AGA-CGA-CCA-GCG-GAA-AT-3'. All dilutions were prepared using a 3×SSC buffer. Following an overnight hybridization of the target sequence, the PC was first rinsed in a 3× buffer solution and then rinsed twice in DI water. The PC was dried under $N_2$ and the final spectrum in each well was recorded.

Figure 11:
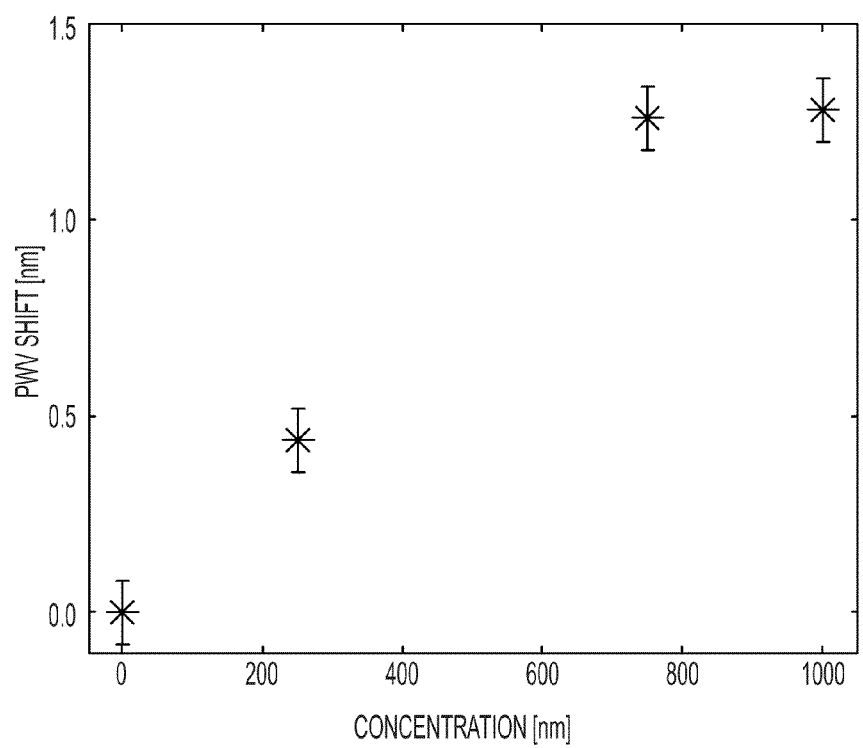
FIG. 11 is a graph showing the shift in PC resonant wavelength as a function of concentration of an oligonucleotide.

FIG. 11 shows the PWV shifts (ΔPWV values) that were measured for the concentrations of 1 μM (well A), 750 nMm (well B) and 250 nMm (well C), as well as a negative control well with no target DNA. The PWV shifts were found to be concentration dependent, generally increasing as a function of increasing concentrations of the target DNA. The standard deviations bars for each concentration in FIG. 11 represent the range of ΔPWV values obtained from measurements taken from two separate locations in each well, representing nonuniformity in the assay process, rather than the noise of the sensor itself.

7. Example Smartphone Fixture for Measuring Reflection Spectra

Figure 12:
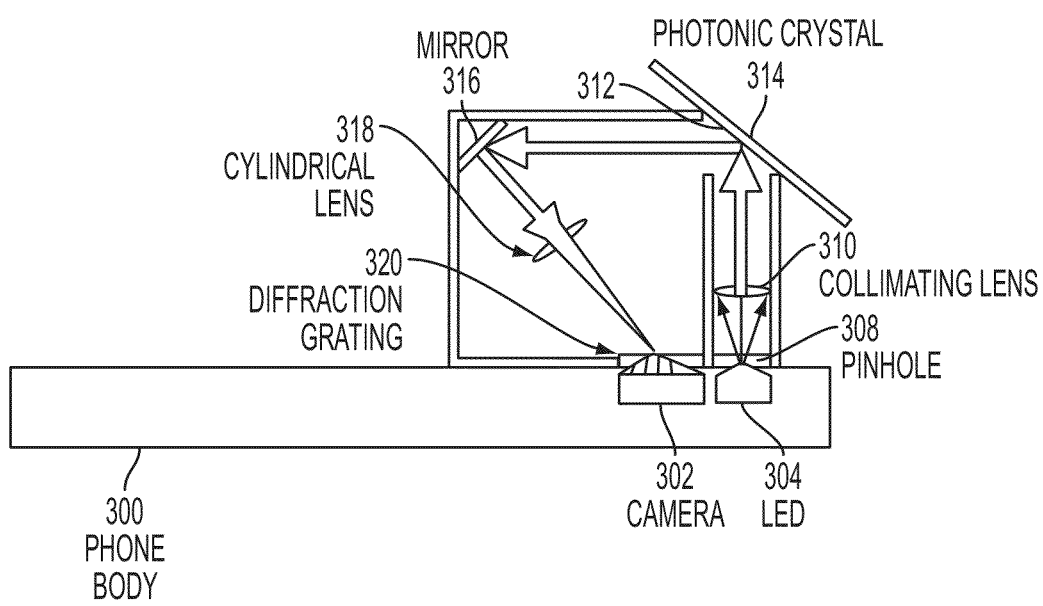
FIG. 12 is schematic diagram of a smartphone mounted to an example fixture for measuring reflection spectra from a PC.

While FIGS. 2A and 2B illustrate an arrangement in which a smartphone detects a spectrum of light transmitted through a PC, it is also possible to use a smartphone to detect a spectrum of light reflected from a PC. FIG. 12 illustrates an example configuration for using a smartphone to obtain a reflection spectrum. This example uses a smartphone 300 that includes a camera 302 (image sensor) and an LED 304 (e.g., a white-light LED intended for flash photography) that is used as the light source. As shown, the smartphone 300 is removably mounted to a fixture that includes a pinhole 308, a collimating lens 310, an opening 312 over which a PC 314 can be placed, a mirror 316, a cylindrical lens 318, and a diffraction grating 320. Light from the LED 304 passes through the pinhole 308 and the collimating lens 310 to reach the PC 314. The light reflected from the PC 314 will be primarily the resonantly reflected wavelengths. The reflected light from the PC 314 is reflected by the mirror 316 so that it passes through the cylindrical lens 318 and diffraction grating 320, which disperses the reflected light into spatially-separated wavelength components that are received by the camera 302. This approach results in a peak in the reflected spectrum, rather than a dip in the transmitted spectrum, which could be easier to measure in the presence of ambient light.

8. Alternative Optical Assay Media

Described above are embodiments in which a PC is used for label-free detection. In other embodiments, label-free detection of biomolecular assays may be achieved using other types of optical assay media. For example, the optical assay medium could include any detection surface that produces a distinct wavelength spectrum when illuminated by a broadband light source could be used in place of the PC. Further, the smartphone could be used to measure shifts in the reflected or transmitted spectra that occurs as a result of adsorption of biomaterial on the detection surface. Alternative detection surfaces can include surface plasmon resonance (SPR) biosensors, resonant waveguide grating biosensors, zero mode waveguide surfaces, metal film over nanoparticle (MFON) surfaces, and many others.

In still other embodiments, the optical assay medium could be configured to perform biomolecular assays with label-based detection. Such label-based biomolecular assays could include, for example, optical absorption assays, surface-based fluorescence assays, solution-based fluorescence assays, fluorescence polarization assays, and assays that use surface-enhance Raman scattering (SERS). These assay types are described in more detail below.

a. Optical Absorption Assays

In optical absorption assays, the presence of an analyte in a test sample results in the generation of a colored product. The concentration of colored product indicates the concentration of the analyte. The concentration of colored product is determined by measuring the optical density of the test sample by illuminating the test sample with a broadband light source and measuring the decreased light intensity transmitted through the sample for the absorption wavelength of the colored product. Thus, the transmitted spectrum will have an absorption feature related to absorption of light by the colored product.

Enzyme-linked immunosorbent assays (ELISA) assays are a class of optical absorption assays. Briefly, a solid surface (such as the surface of a microplate well) is prepared with an antibody that selectively captures an analyte from a test sample. After capture of the analyte, a secondary antibody (recognizing a different location on the analyte than the capture antibody) is applied to the surface. The secondary antibody is linked to an enzyme, and a substrate to that enzyme is introduced to the liquid solution, so that the enzyme-substrate interaction generates colored products. In this process, the enzyme is not consumed, so the amount of colored product will accumulate the longer the interaction is allowed to occur. Based upon this basic principle, several distinct types of ELISA assays have been developed (indirect ELISA, sandwich ELISA, competitive ELISA), which share the detection method of quantifying the optical density of the liquid sample to determine the concentration of colored reaction products. ELISA assays are performed in a transparent container of known dimensions (a "cuvette"), by measuring the intensity of light transmission through the cuvette at specific wavelengths.

Figure 13:
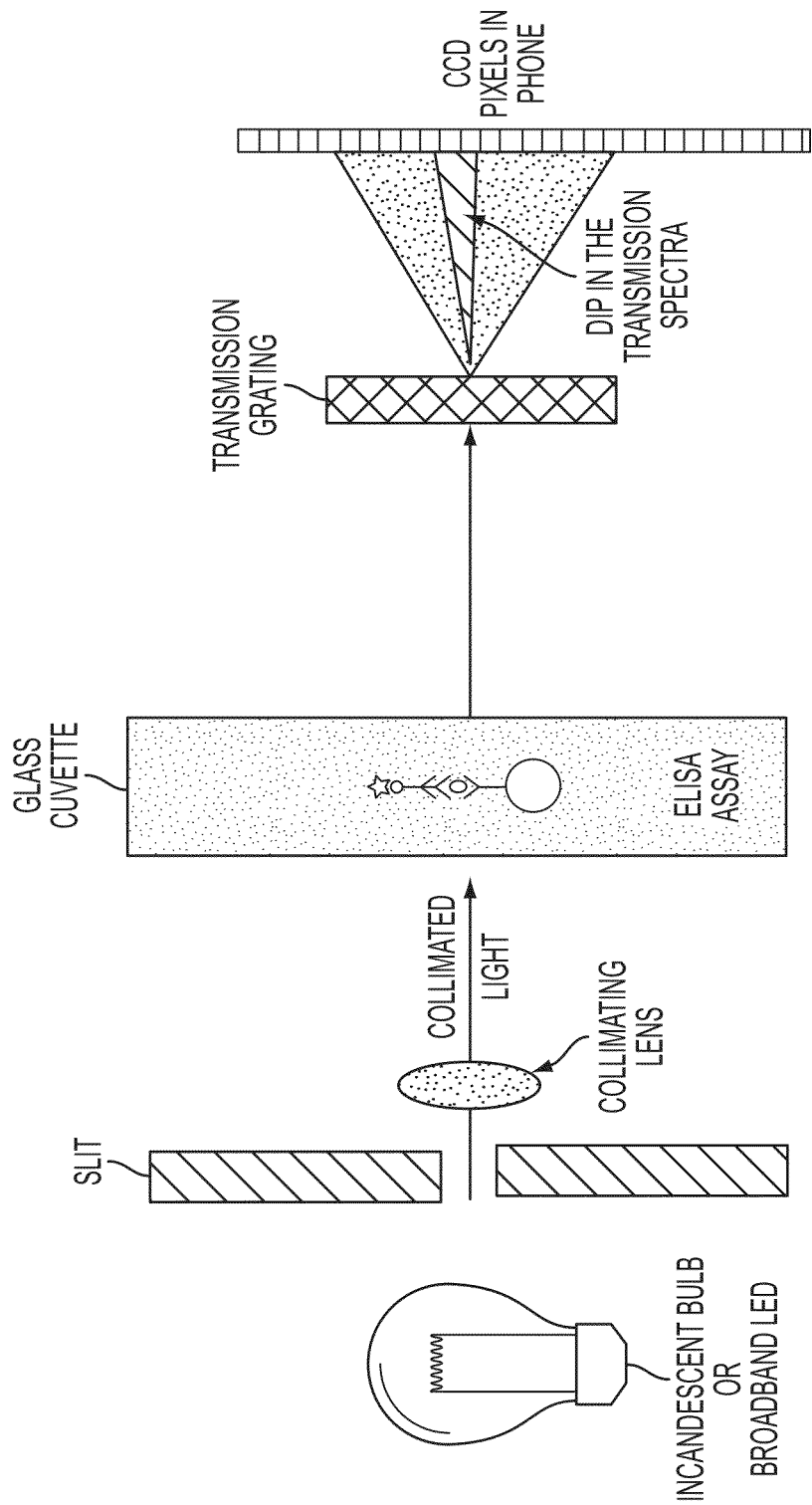
FIG. 13 is a schematic diagram illustrating an example of using a smartphone for detection of an ELISA assay.

FIG. 13 is a schematic diagram of how a smartphone-based spectrometer could be used to measure the optical density of a liquid sample placed in the optical path between a broadband light source, such as an incandescent light bulb or an LED, and a diffraction grating. The diffraction grating disperses the transmitted light into spatially-separated wavelength components that are received by the image sensor (CCD) of a smartphone. A dip in the transmission spectrum is related to absorption of light in the liquid sample and can be used to measure the optical density of the liquid sample. As shown, the optical assay medium includes a glass cuvette that contains a composition for performing an ELISA assay. It is to be understood, however, that the arrangement shown in FIG. 13 could also be used for other optical absorption assays as well.

b. Surface-Based Fluorescence Assays

Figure 14:
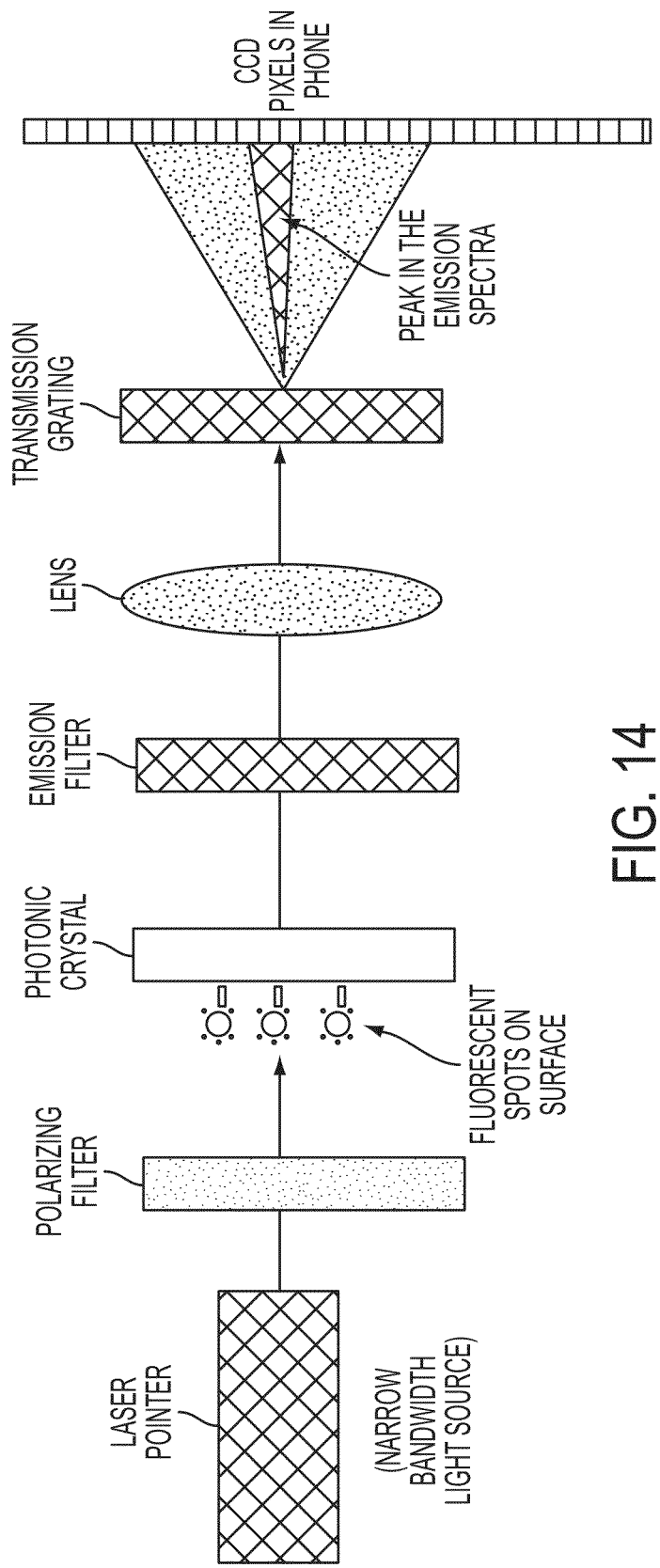
FIG. 14 is a schematic diagram illustrating an example of using a smartphone for detection of a surface-based fluorescence assay.

Fluorophores are often attached to biomolecular or cellular analytes to aid in their detection. When analytes labeled with fluorophores are immobilized upon a solid substrate, the surface density of the labeled analyte can be measured by illuminating with a laser and collecting the fluorescence emission. An example smartphone-based detection system for measuring the fluorescence emission is shown in FIG. 14. In this example, the fluorescently-labeled analyte is immobilized on a PC, though other solid substrates (such as a glass slide) could be used. The PC is illuminated with a laser or other narrowband source with a wavelength that excites the fluorophore so as to cause fluorescence emission. The fluorescence emission is collected by a lens and directed to a diffraction grating. The diffraction grating disperses the transmitted light into spatially-separated wavelength components that are received by the image sensor (CCD) of a smartphone. A peak in the emission spectrum can be used to measure the surface density of the labeled analyte. As shown, an emission filter is used to block the laser wavelength from being received by the image sensor of the smartphone. Alternatively, the laser wavelength may be spatially separated from the wavelength of the fluorescence emission by the diffraction grating and selectively blocked.

Certain solid substrates are capable of enhancing the amount of fluorescence emission detected through the mechanisms of enhanced excitation and/or enhanced extraction. Examples include PC surfaces (as shown in FIG. 14), roughened metal surfaces, zero-mode waveguides, and surfaces exhibiting surface plasmon resonances. In this regard, PC surfaces have been demonstrated as a means for enhancing the detection sensitivity and resolution for assays that use a fluorescent tag to quantify the concentration of an analyte protein molecule in a liquid test sample. PC fluorescent excitation enhancement is obtained by designing the PC structure to provide an optical resonance at the same wavelength as a laser that is used to excite a particular fluorescent dye. Compared to illumination of a fluorophore by a laser on an ordinary glass surface, illumination of a PC by a laser at the resonant coupling condition establishes an electromagnetic standing wave that is confined to the PC surface with a magnitude that is 30-50 times greater than the illumination source. The enhanced electric field extends into the medium (air or water) that is adjacent to the PC, where its intensity decays exponentially to form a ~100 nm deep evanescent field region. The resonant enhancement may be switched on by illuminating the PC with a collimated laser at the resonant coupling angle, and may be switched off by illuminating at a different incident angle.

PC surfaces also offer a second enhancement mechanism called "enhanced extraction." Enhanced extraction is obtained by designing the PC to provide a second optical resonance at the wavelength of fluorescence emission, resulting in a greater proportion of emitted photons being directed near-normal to the PC surface, where they can be gathered efficiently by a detection system. The effects of enhanced excitation and enhanced extraction multiply to result in ~500× overall increase in measured fluorescent intensity on an appropriately designed PC, compared to detection of the same analyte on an unpatterned glass surface.

c. Solution-Based Fluorescence Assays

In addition to surface-based fluorescence assays, a smartphone-based detection system could be used to detect fluorescence emission from fluorescently-labeled analytes in solution. The configuration could be similar to that shown in FIG. 14 but with the solid substrate being substituted with a transparent liquid container that contains the fluorescently-labeled analytes. The transparent liquid container could be, for example, a cuvette or a microfluidic channel with a moving flow of fluorescent-labeled analytes. The system could be used to perform fluorescent resonant energy transfer (FRET) assays in which the binding of biomolecules in solution generates an increase in fluorescence emission from one type of fluorophore (such as an "acceptor" fluorophore) and simultaneous decrease in fluorescence emission from another type of fluorophore (such as a "donor" fluorophore). The system could also be used to detect fluorescence from "molecular beacon" probes, quantum dots, and fluorescent microspheres that are floating in solution.

d. Fluorescence Polarization Assays

Fluorescence polarization (FP) is a homogeneous (liquid-based) assay in which the "polarization" of fluorescence emitted by a fluorophore is measured. The "polarization" (P) is defined by $P=(I_\parallel - I_\perp)/(I_\parallel + I_\perp)$, where $I_\parallel$ and $I_\perp$ represent the fluorescence intensity obtained with the polarizing filter in front of the sensor oriented parallel or perpendicular to the fluorescence excitation polarization. Due to the short (1-20 ns) time delay between excitation and fluorescence emission (called the fluorescent lifetime), larger molecules, which rotate more slowly in solution than smaller molecules, will have a polarization that is closer to that of the excitation.

Briefly, two measurements of fluorescence intensity measured through a linear polarizing filter rotated to orthogonal orientations are used to determine the polarization. When a small molecule that rotates rapidly is bound to a larger molecule, the rotation rate is decreased, resulting in an increase in polarization of the fluorescence emission.

Figure 15:
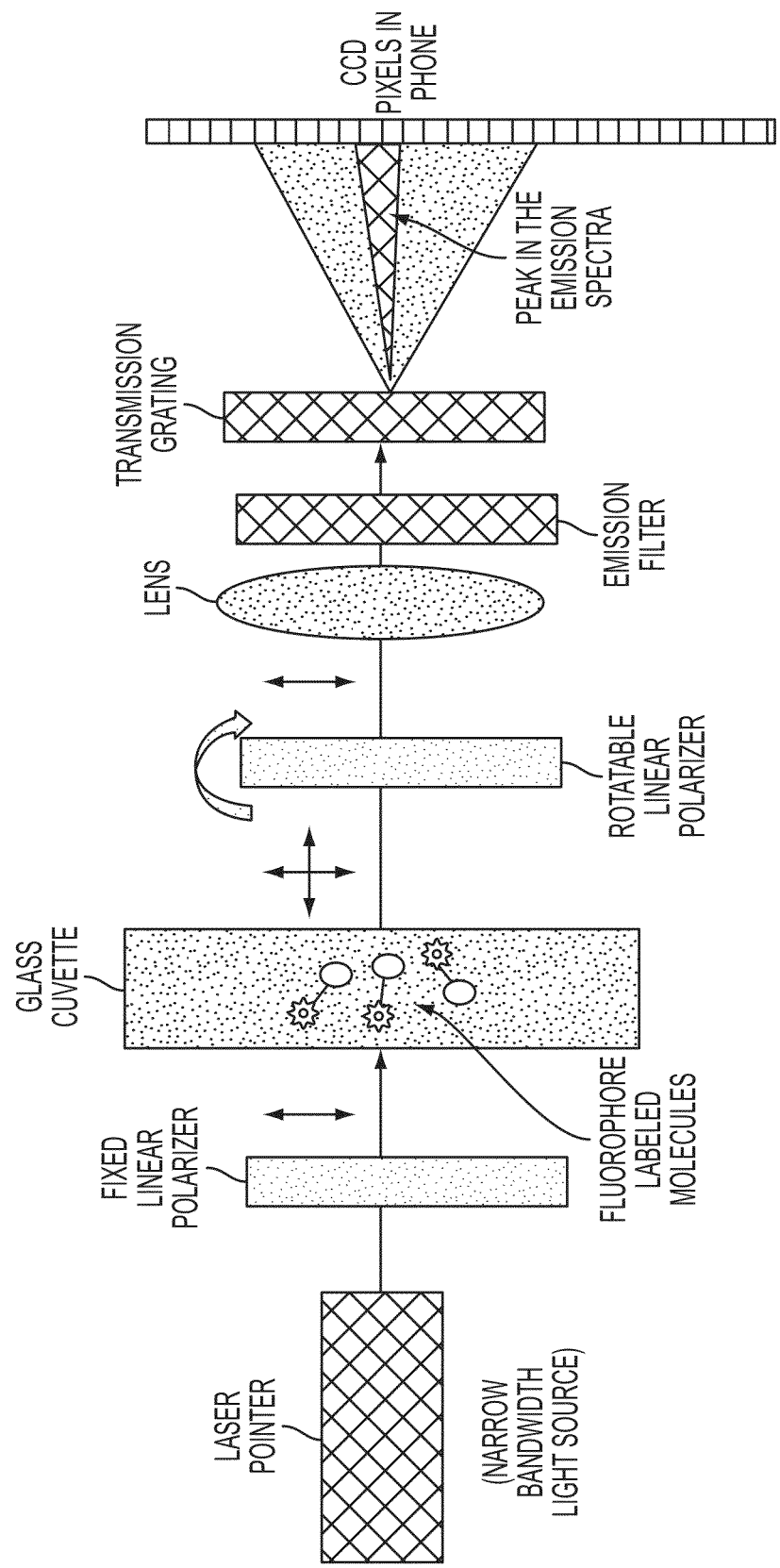
FIG. 15 is a schematic diagram illustrating an example of using a smartphone for detection of a fluorescence polarization assay

An example smartphone-based detection system for measuring the polarization fluorescence emission is shown in FIG. 15. A liquid test sample in a transparent container is placed in the optical path between a laser (excitation) and the smartphone. The light entering the liquid sample is linearly polarized by passing through a polarizing filter, or by using a linearly polarized laser source. A second linearly polarized filter is placed on the distal end of the sample which may be switched between two polarization states. Fluorescence emission is collected by a lens and directed to a diffraction grating. The diffraction grating disperses the transmitted light into spatially-separated wavelength components that are received by the image sensor (CCD) of a smartphone. Measurements of fluorescence intensity are taken with the switchable polarization filter oriented in alignment with the first linear polarizer and orthogonal to the first linear polarizer.

e. Surface-Enhanced Raman Scattering (SERS)

In SERS assays, the analyte binds to Raman reporter molecules that are on a nanostructured surface that is capable of enhancing surface electric fields from an incident laser source. The surface-enhancement can increase the intensity of Raman scattering by many orders of magnitude. A smartphone-based detection system for measuring the Raman scattering can be similar to that shown in FIG. 14, but with a SERS surface taking the place of the PC and Raman reporter molecules taking the place of the fluorophores. Alternatively, a reflection configuration could be used.

9. Example Multimode Instrument

Figure 16:
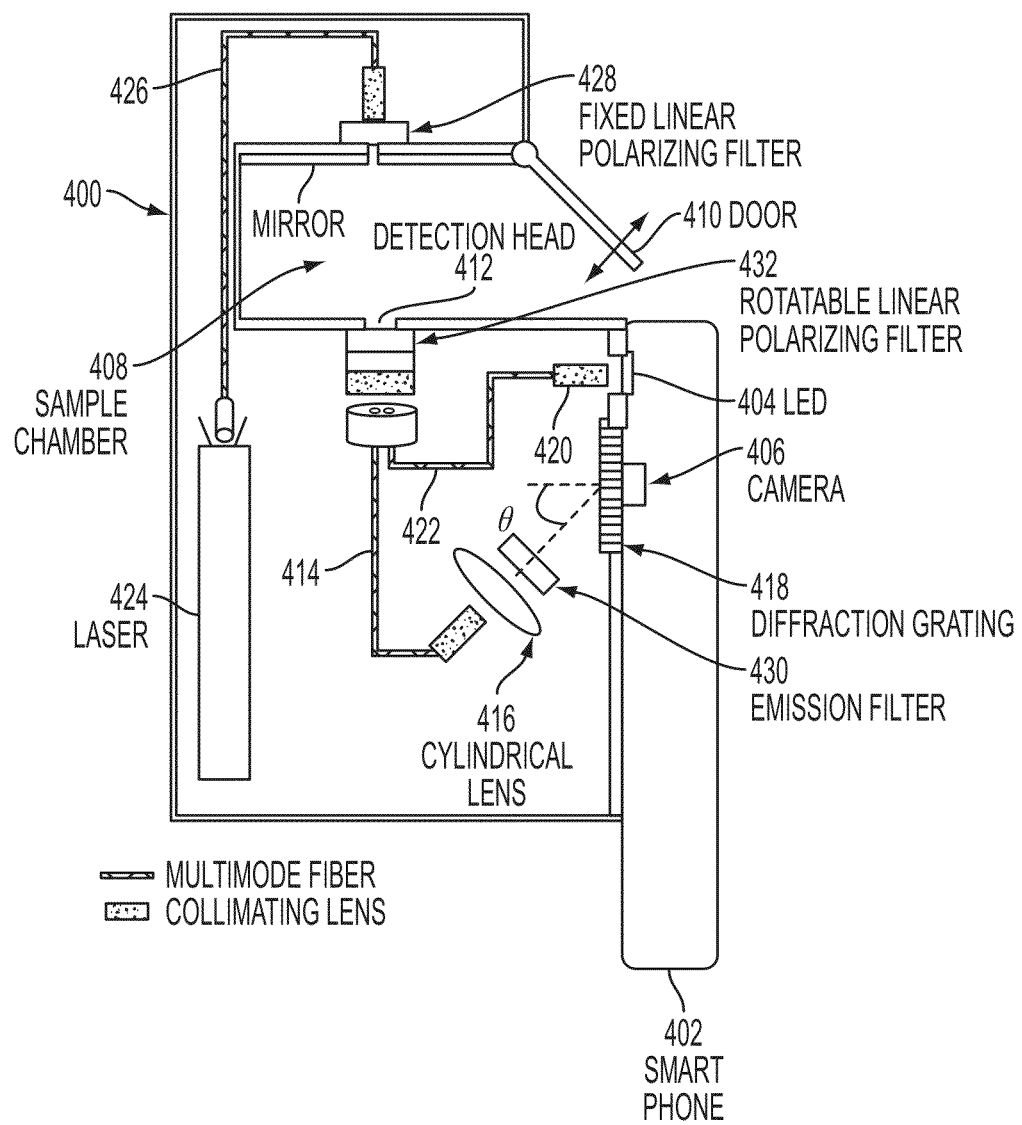
FIG. 16 is a schematic diagram showing a smartphone mounted to an example multimode instrument.

A smartphone could be coupled to an instrument that is capable of performing multiple different types of biomolecular assays, such as any of the assay formats described above. FIG. 16 illustrates an example in which a multimode instrument 400 is coupled to a smartphone 402. The smartphone 402 includes an LED 404 and a camera 406. The camera 406 includes an image sensor, such as a CCD. The instrument 400 includes a sample chamber 408 for receiving an optical assay medium. The optical assay medium could include a PC, a cuvette, or other components depending on the type of optical assay being performed. The sample chamber 408 may include a door 410 that prevents stray light from entering.

The optical assay medium may be positioned over a detection head 412 in the sample chamber 408. The instrument 400 may include an optical output path for receiving an optical output from the optical assay medium in the sample chamber 408 via the detection head 412. The optical output path may include a multimode fiber 414 that directs light from the detection head 412 to a cylindrical lens 416. The optical output path may further include a wavelength-dispersive element, such as a diffraction grating 418, that is configured to disperse the optical output into spatially-separated wavelength components. The optical output path may also include other optical components, such as collimating lenses, filters, and polarizers.

The instrument 400 can include a mount for removably mounting the smartphone 402 in a working position such that the camera 406 is optically coupled to the optical path, for example, in a predetermined position relative to the diffraction grating 418. In this working position, the camera 406 can receive at least a portion of the dispersed optical output such that different locations are received at different locations on the image sensor.

The instrument 400 may also include an input optical path for directing light from a light source to the optical assay medium in the sample chamber 408, for example, through the detection head 412. In some instances, the LED 404 on the smartphone 402 could be used as the light source. To use the LED 404 as the light source, the input optical path may include a collimating lens 420 that receives light from the LED 404 when the smartphone is mounted to the instrument 400 in the working position. The input optical path may further include a multimode fiber 422 that directs the light from the collimating lens 420 to the detection head 412. The input optical path may also include other optical components, such as collimating lenses, filters, and polarizers.

The instrument 400 may also include an additional input optical path that directs light form an internal light source, such as a laser 424, to the optical assay medium in the sample chamber 408. The additional input optical path may include a multimode optical fiber 426, as well as collimating lenses, filters, polarizers, or other optical components.

For label-free assays (e.g., using a PC) and optical absorption assays (e.g., ELISA assays), the LED 404 may be used as the light source. For fluorescence-based assays, laser 424 may be used as the light source, and a fixed linear polarizer 428 may be included in the input optical path. An emission filter 430 may also be included in the output optical path to filter out the wavelength of the laser 424. For fluorescence polarization assays, a rotatable linear polarizer 432 may also be included in the output optical path.

The sample chamber 408 may be able to accommodate both homogeneous and heterogeneous assays. In some examples, homogeneous assays (such as ELISA, FRET, and FP) may be performed in a transparent 1.5 mL disposable cuvette that is inserted into the sample chamber 408 for one-at-a-time analysis. In some examples, heterogeneous assays (PC biosensor, surface-based FRET) may be performed in a cartridge containing 16 independent wells that be measured in series by sliding the cartridge in fixed increments across the detection head 412. For enhancement of fluorescence emission, a PC may be incorporated into the internal surface of the cuvette (for homogeneous assays) or the surface of a microscope slide (for heterogeneous assays).

The smartphone 402 can run an application for use with instrument 400. The application may be used to perform such functions as system calibration (including wavelength and intensity calibration), prompting a user through assay steps, gathering optical data, performing image processing, and reporting results. The application can lead an untrained user through the process of performing the assay correctly and can reduce the likelihood of user error leading to false positive or false negative assay results.

The application could also combine assay results with other sources of sensor data from the smartphone, such as images, video, audio recordings, location, and date/time. The application may be able to securely communicate results to user-specified servers, for example, to deliver results to a patient's physician. The results could also be collected in a database for additional analysis, such as developing statistics or identifying disease outbreaks.

10. Conclusion

Example embodiments have been described. It is to be understood, however, that variations of these embodiments, as well as additional embodiments, are possible within the scope of the claims set forth below.

What is claimed is:

1. A system, comprising:

a mobile computing device, wherein the mobile computing device includes an image sensor, a light source, a processor, and a memory that stores program instructions;

an optical instrument, comprising:

a sample chamber for receiving an optical assay medium, wherein the sample chamber comprises a door that prevents stray light from entering;

an input optical path for directing light from the light source to the optical assay medium in the sample chamber, wherein the input optical path comprises a first multimode fiber;

an output optical path for receiving an optical output from the optical assay medium in the sample chamber, wherein the output optical path comprises a second multimode fiber and a wavelength-dispersive element configured to disperse the optical output into spatially-separated wavelength components; and a mount for removably mounting the mobile computing device to the instrument in a fixed position relative to the wavelength-dispersive element, wherein in the fixed position the image sensor of the mobile computing device is optically coupled to the output optical path such that the image sensor receives at least a portion of the dispersed optical output and different wavelength components are received at different locations on the image sensor, wherein the program instructions stored in the memory are executable by the processor to cause the mobile computing device to perform functions, the functions comprising:

using the image sensor to obtain a plurality of images of the portion of the dispersed optical output; and determining a wavelength spectrum of the optical output based on the plurality of images.

2. The system of claim 1, wherein the mobile computing device is a smartphone.

3. The system of claim 1, wherein the light source is a broadband light source.

4. The system of claim 3, wherein the broadband light source is a light emitting diode (LED).

5. The system of claim 1, wherein the optical assay medium comprises a transparent container containing a composition for performing an enzyme-linked immunosorbent assay (ELISA) that produces a colored product in the presence of an analyte.

6. The system of claim 5, wherein the optical output comprises light from the light source transmitted through the container and has a wavelength spectrum with an absorption feature related to absorption of light by the colored product.

7. The system of claim 6, wherein an intensity of the absorption feature is indicative of a result of the ELISA.

8. The system of claim 1, wherein the mobile computing device further includes a display and wherein the functions further comprise: displaying an indication of the wavelength spectrum of the optical output on the display.

9. The system of claim 1, wherein the mobile computing device further includes a display and wherein the functions further comprise: determining a result of a biomolecular assay based on the wavelength spectrum of the optical output; and displaying an indication of the result on the display.

10. The system of claim 1, wherein the wavelength-dispersive element is a diffraction grating.

11. The system of claim, wherein in the fixed position a user interface of the mobile computing device is accessible.

* * * * *